(12) United States Patent
Gilon et al.

(10) Patent No.: US 11,267,846 B2
(45) Date of Patent: Mar. 8, 2022

(54) HIGH SHEAR SOLID PHASE SYNTHESIS

(71) Applicant: YISSUM RESEARCH DEVELOPMENT COMPANY OF THE HEBREW UNIVERSITY OF JERUSALEM LTD., Jerusalem (IL)

(72) Inventors: Chaim Gilon, Jerusalem (IL); Moshe Bentolila, Moshav Tekuma (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 16/979,212

(22) PCT Filed: Mar. 12, 2019

(86) PCT No.: PCT/IL2019/050271
§ 371 (c)(1),
(2) Date: Sep. 9, 2020

(87) PCT Pub. No.: WO2019/175867
PCT Pub. Date: Sep. 19, 2019

(65) Prior Publication Data
US 2020/0399306 A1    Dec. 24, 2020

Related U.S. Application Data

(60) Provisional application No. 62/642,016, filed on Mar. 13, 2018.

(51) Int. Cl.
*B01J 19/00* (2006.01)
*B01J 19/18* (2006.01)
*C07K 1/04* (2006.01)

(52) U.S. Cl.
CPC ............... *C07K 1/045* (2013.01); *B01J 19/00* (2013.01); *B01J 19/0046* (2013.01)

(58) Field of Classification Search
CPC ........ B01J 19/00; B01J 19/0046; B01J 19/18; C07K 1/00; C07K 1/04; C07K 1/045
See application file for complete search history.

(56) References Cited

U.S. PATENT DOCUMENTS 6,028,172 A    2/2000 Stepaniuk
6,291,669 B1   9/2001 Kwiatkowski
(Continued)

FOREIGN PATENT DOCUMENTS

CN    1966515 A     5/2007
EP    0042792 A1   12/1981
(Continued)

OTHER PUBLICATIONS

Jolley et al., Highly Productive Continuous Flow Synthesis of Di- and Tripeptides in Water, Aug. 30, 2017, ACS Publications, Org. Process Res. Dev. 2017, 21, 1557-1565 (Year: 2017).*

(Continued)

*Primary Examiner* — Natasha E Young
(74) *Attorney, Agent, or Firm* — J.A. Lindeman & Co., PLLC; Aaron Raphael

(57) ABSTRACT

The present disclosure relates to solid phase synthesis of organic molecules and particularly to highly efficient methods for synthesizing polymers, such as peptides, nucleotides or saccharides, employing solid phase synthesis.

20 Claims, 7 Drawing Sheets

(56) References Cited

U.S. PATENT DOCUMENTS

| | | | |
|---|---|---|---|
| 6,320,025 B1 | 11/2001 | Slavazza | |
| 7,132,531 B1 * | 11/2006 | Wellings | B01F 7/242 536/25.3 |
| 2006/0223816 A1 | 10/2006 | Adin | |

FOREIGN PATENT DOCUMENTS

| | | |
|---|---|---|
| EP | 0503683 A1 | 9/1992 |
| WO | 0066258 A2 | 11/2000 |
| WO | 2008080845 A1 | 7/2008 |

OTHER PUBLICATIONS

Renil et al., PEGA Supports for Combinatorial Peptide Synthesis and Solid-phase Enzymatic Library Assays, 1998, Journal of Peptide Science, 4, 195-210 (Year: 1998).*

Gordon, The renascence of continuous-flow peptide synthesis—an abridged account of solid and solution-based approaches, 2018, Org. Biomol. Chem., 16, 180-196 (Year: 2018).*

Alshanski et al., (2018) Enhancing the Efficiency of the Solid Phase Peptide Synthesis (SPPS) Process by High Shear Mixing. Organic Process Research & Development 22(9): 1318-1322.

Amblard et al., (2006) Methods and protocols of modern solid phase peptide synthesis. Mol Biotechnol 33: 239-254.

Basu et al., (1999) Consider a New Approach to Pharmaceutical Process Development. Chemical engineering progress 95(8): 82-90.

Ben Tolila et al., Introduction of CAPE into an Active Pharmaceuticals Ingredients Company. 18th European Symposium on Computer Aided Process Engineering (ESCAPE 18); Lyon, France Jun. 1-4, 2008.

Bentolila et al., (2018) Optimization of Chemical Processes by the Hydrodynamic Simulation Method (HSM). ChemEngineering 2(2): 21; 8 pages.

Berty (1979) The Changing Role of the Pilot Plant. Chem Engng Progr 75(9): 48-51.

Bikshapathy and R Nagaraj (1997) Manual solid-phase syntheses of peptides on resins with high loading capacity requiring small volumes of solvents. Proc Indian Acad Sci (Chem Sci) 109(5): 319-323.

Bonkowski et al., (2013) Basic Concepts of using Solid Phase Synthesis to Build Small Organic Molecules using 2-Chlorotrityl Chloride Resin. Mod Chem appl 1: 113; 4 pages.

Brown et al., (1998) Solid Phase Synthesis. Synlett 1998(8): 817-827.

Coantic et al., (2008) Microwave-assisted Solid Phase Peptide Synthesis on High Loaded Resins. Int J Pept Res Ther 14: 143-147.

Collins et al., (2014) High-Efficiency Solid Phase Peptide Synthesis (HE-SPPS). Org Lett 16(3): 940-943.

Edelstein et al., (1986) Design considerations for pilot scale solid phase peptide synthesis reactors. Chemical Engineering Science 41(4): 617-624.

Falb et al., (1999) In situ generation of Fmoc-amino acid chlorides using bis-(trichloromethyl)carbonate and its utilization for difficult couplings in solid-phase peptide synthesis. The Journal of Peptide Research 53(5): 507-517.

Furka et al., (1991) General method for rapid synthesis of multicomponent peptide mixtures. International Journal of Peptide and Protein Research 37(6): 487-493.

Genck et al., (2011) Computer aided process engineering at chemagis. Reprinted from Pharm Eng 31(4); 8 pages.

Gude et al., (2002) An accurate method for the quantitation of Fmopc-derivatized solid supports. Lett Pept Sci 9: 203-206.

Henninot et al., (2018) The Current State of Peptide Drug Discovery: Back to the Future? J Med Chem 61(4): 1382-1414.

Khattab et al., (2015) Peptide Coupling Reactions. J Mol Pharm Org Process Res 3(1): e119; 2 pages.

König and Geiger (1970) Eine neue Methode zur Synthese von Peptiden: Aktivierung der Carboxylgruppe mit Dicyclohexycarbodiimid unter Zusatz von 1-Hydroxy-benzotriazolen [A new method for synthesis of peptides: activation of the carboxyl group with dicyclohexylcarbodiimide using 1-hydroxybenzotriazoles as additives]. Chem Ber 103(3): 788-798 Abstract.

Kresta et al., (2001) Internal annular wall jets: Radial flow in a stirred tank. AIChE Journal 47(11): 2390-2401.

Lax (2010) The Future of Peptide Development in the Pharmaceutical Industry. PharManufacturing: The International Peptide Review 2010: 10-15.

Levenspiel (1999) Chemical Reaction Engineering. Ind Eng Chem Res 38(11): 4140-4143.

Merrifield (1963) Solid Phase Peptide Synthesis. I. The Synthesis of a Tetrapeptide. J Am Chem Soc 85(14): 2149-2154.

Merrifield (1964) Solid-Phase Peptide Synthesis. III. An Improved Synthesis of Bradykinin*. Biochemistry 3(9):1385-1390.

Merrifield (1985) Solid Phase Synthesis (Nobel Lecture). Bioscience Report 5: 353-376.

Merrifield (1986) Solid phase synthesis. Science 232(4748): 341-347.

Metzner and Otto (1957) Agitation of non-Newtonian fluids. AIChE Journal 3(1): 3-10.

Montalbetti and Falque (2005) Amide bond formation and peptide coupling. Tetrahedron 61: 10827-10852.

Ng and Wibowo (2003) Beyond process design: The emergence of a process development focus. Korean J Chem Eng 20: 791-798.

Pattabiraman and Bode (2011) Rethinking amide bond synthesis. Nature 480(7378): 471-479.

Sánchez Pérez et al., (2006) Shear rate in stirred tank and bubble column bioreactors. Chemical Engineering Journal 124(1-3): 1-5.

Seeberger and Haase (2000) Solid-Phase Oligosaccharide Synthesis and Combinatorial Carbohydrate Libraries. Chem Rev 100(12): 4349-4394.

Sheehan and Hess (1955) A New Method of Forming Peptide Bonds. J Am Chem Soc 77(4): 1067-1068.

Edwards and Baker, Chapter 7—A review of liquid mixing equipment; Edwards, Baker and Godfrey, Chapter 8—Mixing of liquids in stirred tanks; Bourne, Chapter 10—Mixing in single-phase chemical reactors; Nienow, Chapter 16—The suspension of solid particles. Butterworth-Heinemann 1997. In: Mixing in the Process Industries. Edited by: Harnby N, Edwards MF and Nienow AW. pp. 118-136, 137-158, 184-199, 364-393.

Peptide Synthesis and Purification. Systems and Accessories. Biotage, 2013. 24 pages.

* cited by examiner

HIGH SHEAR SOLID PHASE SYNTHESIS

This application is a national stage application of International Application No. PCT/IL2019/050271, now WO 2019/175867, filed on Mar. 12, 2019, which claims the benefit of U.S. Provisional Application No. 62/642,016, filed Mar. 13, 2018, the entire contents of which are incorporated herein by reference.

TECHNICAL FIELD

The present disclosure generally relates to the field of solid phase synthesis and methods for synthesizing peptides and other molecules employing solid phase synthesis.

BACKGROUND

There are many applications of peptide drugs. There are about 100 approved peptide drugs on the market among them several blockbusters such as the somatostatin analog octreotide. The most popular and dominant segments of peptide drugs include HIV treatment, diabetes, cancer treatment, with applications in the fields of neurological disorders, such as Alzheimer's and Parkinson's disease, as well as autoimmune diseases, such as Lupus, Rheumatoid Arthritis and Uveitis also constantly arising.

Three main methods are used to prepare large quantities of peptides in the pharmaceutical industry: recombinant technologies; solution phase chemical synthesis; and solid phase peptide synthesis (SPPS). SPPS is the manufacturing procedure of choice for peptides due to the low cost of raw materials and economy of scale. Solid-phase chemistry approaches are faster and less expensive for manufacturing from gram to 100 Kg scale of relatively short peptides (typically up to about 50 amino-acid long) and are better suited to early stage clinical development.

The SPPS process is a multi-step chain process involving two main types (i.e. stages or steps) of reactions: (i) removal of temporary protecting group (deprotection) and (ii) coupling of an amino acid. These reactions take place sequentially one after the other, with an intermediate washings taking place for removal of unreacted reagents and soluble side- and by-products. In general, in solid phase syntheses a sequence of building blocks is constructed over an insoluble polymeric resin having linking units reactive towards the building blocks. Since some building blocks, such as amino acids comprise at least two functional groups reactive towards one another (i.e. the amino and carboxylate groups), one group, typically the amino group is protected beforehand, such that the free carboxylate group reacts with the linking unit, rather than with another present amino acid. For continuation of the amino acid chain, deprotection of the amino groups is preformed, thereby producing a resin having the first amino acid, free for reaction with the consecutive N-protected amino acid. The process repeats until a desired number of building blocks is achieved. The purpose of using an insoluble resin is to enable easy workup procedure of simply washing all excess soluble reagents, as well as side- and by-products, while remaining with the desired product attached to the insoluble resin. The last synthetic step is, therefore, removing the side-chain protecting groups and cleaving the building block chain (the peptide) and isolating it from the insoluble resin.

Thus, solid phase syntheses of a polymeric molecule, typically include the following synthetic steps: (a) swelling of functionalized resin polymeric beads; (b) coupling a first protected monomeric unit to the functionalized resin; (c) washing the excess of the first protected monomeric unit; (d) deprotecting the resin linked to the first monomer formed in step (b) using a deprotection reagent, thereby forming a resin linked to the first deprotected monomer; and (e) washing the excess of the deprotection reagent. Steps (b)-(e) are then cyclically repeated, with the subsequent protected monomers, thereby forming resin-polymer molecule. Thus, steps (b)-(e) are regarded as cycles, where the total solid phase synthesis typically includes a plurality of cycles. Lastly, the desired product molecule is cleaved from the resin and is separate therefrom, thereby obtaining the final polymeric product.

The resin used for solid-phase synthesis is typically an insoluble polymer, modified with chemically reactive functional groups. These functional groups are chemically suitable to be coupled with a first monomer, which is to be incorporated into the target product oligomer/polymer. Said first monomer, as well as the other sequential monomers, typically includes at least two functional groups, which are reactive towards one another. However, the placement of protecting group on one of these functional groups restricts the transformation to coupling of the protected monomeric unit into the resin, thereby forming a resin, which is initially linked to the first monomer; and after a number of similar cycles, linked to a construct of monomers. Typically each protected monomer in the sequence of cycles is used in excess (with respected to the resin-bound molecules) for ensuring the completion of the reaction. Typically the deprotection reagent is also used in excess (with respected to the resin-bound monomer molecules) for ensuring the completion of the reaction.

Since the invention of SPPS by Bruce Merrifield in 1963 (Merrifield, R. B. (1963) J. Am. Chem. Soc. 85, 2149-2154) many methods were introduced to improve that technique. Most of these methods are based on chemical modification of coupling reagents (Pattabiraman et al. Nature (2011) 480, 471-479). Other improvements include thermal methods e.g. microwave and heating (Collins et al. (2014) Org. Lett. 16, 940-943). Nevertheless, very few investigations were made on the influence of the hydrodynamic parameters on the yield and side reactions in SPPS.

Secondary and tertiary structures of polypeptides are particularly sensitive to shearing forces. When exposed to shear, the secondary and/or tertiary structure of a peptidic molecule can be irreversibly altered, potentially resulting in loss of biological activity. The primary structure, i.e., the amino acid sequence, may be also destroyed or interrupted if the peptidic molecule is subjected to sufficient shear force. Considering that, method of synthesizing peptides generally utilizes procedures that minimize the exposure of peptidic molecules to shear stress. For example, EP0503683 discloses a "vortex" agitation mode that prevents resin agglomeration and allows total fluid-resin interaction without the use of impeller type mechanical agitation. According to this publication, with mechanical agitation, the shear and resin abrasion caused by the impeller can fracture the resin beads into smaller and smaller particles which can eventually clog the filters, thus forcing interruption of the synthesis process. With the vortex agitator there are no impeller type shear or abrasive effects on the resin beads.

In his seminal paper (Merrifield, R. B. (1963) J. Am. Chem. Soc. 85, 2149-2154) Merrifield used a magnetic stirrer for mixing the beads of polymeric resin. It turned out that this method breaks the resin bead to small particles that blocks the sinter glass filter and prevent filtration. To avoid this problem Merrifield invented a manually operated apparatus consisting of a reaction vessel, in which the reactants are mixed by shaking rather than by stirring (Merrifield, R. B. Solid Phase Synthesis (Nobel Lecture), Angewandte Chemie International Edition (1985) 24, 799-892). Since then, production of peptides is generally restricted to employing gentle mixing methods, such as vortex, nitrogen stream, rotation in rotary evaporator rotors, agitation by rocking etc. In large scale Solid phase synthesis (SPS) glass reactors are typically employed with a mechanical stirrer at low rpm for gentle agitation of the resin beads. The impeller of such stirrer is specially designed for agitation with very low sheer rate.

Solid phase synthesis is routinely used for synthesis of peptides and polypeptides. Nevertheless, this method is by no means restricted to syntheses of such compounds, and the preparations of other oligomeric/polymeric molecules, such as modified peptides, peptidomimetics, oligonucleotides, peptide nucleic acid molecules, oligosaccharides and small organic molecules were achieved through solid phase synthesis. Generally, any organic polymer or molecule that requires selective protection/deprotection, coupling and cleavage steps may be synthesized through solid phase synthesis (for example Boncher et al. (2013) Mod. Chem appl. 1:113).

Solid phase oligonucleotide synthesis is typically implemented using the phosphoramidite method. In this method phosphoramidite building blocks derived from protected 2'-deoxynucleosides ribonucleosides or chemically modified nucleosides. To obtain the desired oligonucleotide, the building blocks are sequentially coupled to the growing oligonucleotide chain in the required order. The building blocks involved in this method are 3'-O—(N,N-diisopropyl phosphoramidite) derivatives of nucleosides (nucleoside phosphoramidites). Generally, a resin having an O-protecting group is deprotected and coupled with an O-protected nucleoside phosphoramidite to form a P—O bond (where the phosphorus is originated from the added building block and the oxygen is originally part of the resin-bound reactant). The next step typically involves capping of unreacted O-terminated resin, for suppressing formation of side products. Next, the phosphorus atom is oxygenated and the oxygen deprotected, such that the product is reactive towards a further building block. Upon the completion of the chain assembly, the product is released from the solid phase to solution, deprotected, and collected. Typically, synthetic oligonucleotides are single-stranded DNA or RNA molecules of around 15-25 bases in length.

The solid phase synthesis of oligosaccharides is more diverse, as sugar units (i.e. monosaccharide units) may be connected to one another through a variety of C—O linkages in different positions of the sugar ring. However, oligosaccharide SPS strategies share with the other SPS methodologies the common feature of repeating deprotecting-coupling cycles. Seeberger and Haase (Chem. Rev., 2000, 100 (12), pp 4349-4394) summarize different oligosaccharide SPS processes.

There is an unmet need for improved methods for synthesizing peptides in large scale with higher efficiency and speed and lower side-reactions.

SUMMARY OF THE INVENTION

The present invention provides improved methods of solid phase synthesis of oligomers, such as peptides, oligosaccharides, oligonucleotides and other molecules. The invention is based in part on the unexpected finding that solid phase synthesis using high shear forces and steering speed, do not harm the solid support or synthesized molecules but improves synthesis efficiency such as synthesis time, yield and purity.

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to one aspect, the present invention provides a method for solid phase stepwise synthesis of organic molecules, comprising at least one mixing step which involves employment of high shear force within the synthesis mixture, wherein a solid-phase resin is in contact with a stirring apparatus at all synthesis steps of the stepwise synthesis.

According to some embodiments, the method comprises the steps: providing a reactor comprising a reaction chamber and a stirring apparatus comprising an impeller having at least two blades rotatable about an axis; inserting beads of functionalized polymeric resin and at least one solvent into the reactor to provide a reaction mixture, wherein the reaction mixture is in contact with the rotatable blades; inserting at least one reactant into the reaction chamber; and spinning the impeller for a period of time, at a rotational rate of at least 600 rounds per minute, while maintaining a sheer rate of at least $3 \cdot 10^3$ $\sec^{-1}$ thereby performing at least one step of the solid phase synthesis.

According to some embodiments, the stirring apparatus is a mechanical stirrer and spinning of the impeller is performed at a rotational rate of 600 to 1000 rounds per minute, maintaining a sheer rate of at least $3 \cdot 10^3$ $\sec^{-1}$.

According to other embodiments, the stirring apparatus is a homogenizer and spinning of the impeller is performed at a rotational rate of 5,000-30,000 rounds per minutes while maintaining a shear rate of at least $1 \cdot 10^6$ $\sec^{-1}$.

A stirring apparatus according to the invention is a stirrer, such as a mechanical stirrer or a homogenizer, comprising at least two rotatable blades. Any stirrer that is capable to being used to stir a solid phase synthesis reaction and create rotational rate and shear rate indicated above, may be used of according to the present invention.

According to some embodiments, the homogenizer is a rotor-stator homogenizer.

According to some embodiments, the stirring apparatus and the reaction chamber are substantially coaxial. According to some embodiments, the mechanical stirrer and the reaction chamber are substantially coaxial. According to some embodiments, the homogenizer and the reaction chamber are substantially coaxial.

According to some embodiments, any of the stirring apparatuses disclosed herein, such as mechanical stirrers or homogenizers, comprise a generally elongated body, which align along an axis. The reaction chamber, according to some embodiments, is three dimensional and includes an open edge for the insertion of the stirring apparatus. According to some embodiments, the open edge is two dimensional, such that the stirring apparatus is inserted through a location substantially in the center of the open edge. In such manner, the reaction chamber and the or homogenizer are substantially coxial, according to some embodiments.

The term "solid phase synthesis" (SPS) means one or a series of chemical reactions used to prepare either a single compound or a library of molecularly diverse compounds, wherein the chemical reactions are performed on a compound that is bound to a solid phase support material through an appropriate linkage. Thus, according to the solid phase synthesis synthetic approach the compound or a precursor thereof is attached to a solid support during some or all of the synthetic steps. SPS is regularly implemented in the production of peptides, polysaccharides and polynucleotides.

According to some embodiments, the organic molecule formed in the method is a polymeric organic molecule.

According to some embodiments, the method comprises the steps:
(a) providing a reactor comprising a reaction chamber and a stirring apparatus comprising an impeller having at least two blades rotatable about an axis;
(b) inserting beads of functionalized polymeric resin and at least one solvent into the reactor to provide a reaction mixture, wherein the reaction mixture is in contact with the rotatable blades;
(c) inserting at least one protected monomeric organic molecule into the reaction chamber and spinning the impeller and at least one coupling agent, thereby forming a coupling product of the protected monomeric organic molecule and the resin;
(d) washing excess of said protected monomeric organic molecule; and
(e) inserting at least one deprotecting reagent into the reaction chamber and spinning the impeller, thereby removing at least one protecting group from the coupling product, forming a coupling product of a deprotected monomeric organic molecule and the resin, thereby completing a cycle in the solid phase synthesis of a polymeric organic molecule;
wherein the spinning of the impeller in at least one of steps (c) and (e) is performed for a period of time, at a rotational rate of at least 600 rounds per minute, while maintaining a sheer rate of at least $3 \cdot 10^3$ sec$^{-1}$, optionally wherein steps (c) to (e) are repeated a plurality of cycles.

According to some embodiments, there is provided a method for performing at least one cycle in the solid phase synthesis of a polymeric organic molecule, the method comprising the steps of:
(a) providing a reactor comprising a reaction chamber and a stirring apparatus, wherein the stirring apparatus comprises an impeller having at least two blades rotatable about an axis;
(b) inserting beads of functionalized polymeric resin and at least one solvent into the reactor to provide a reaction mixture, wherein the reaction mixture is in contact with the rotatable blades;
(c) inserting at least one protected monomeric organic molecule at least one coupling agent into the reaction chamber and spinning the impeller, thereby forming a coupling product of the protected monomeric organic molecule and the resin;
(d) washing excess of said protected monomeric organic molecule; and
(e) inserting at least one deprotecting reagent into the reaction chamber and spinning the impeller, thereby removing at least one protecting group from the coupling product, forming a coupling product of a deprotected monomeric organic molecule and the resin, thus completing a cycle in the solid phase synthesis of the polymeric organic molecule;
wherein the spinning of the impeller in at least one of steps (c) and (e) is performed for a period of time, at a rotational rate of at least 600 rounds per minute, while maintaining a sheer rate of at least $3 \cdot 10^3$ sec$^{-1}$, optionally wherein steps (c) to (e) are repeated a plurality of cycles.

According to some embodiments, the method further comprises a step of washing an excess of said deprotecting reagent, thereby isolating the coupling product of a deprotected monomeric organic molecule and the resin.

According to some embodiments, step (d) comprises washing excess of said protected monomeric organic molecule thereby separating the excess of said protected monomeric organic molecule from the coupling product of the protected monomeric organic molecule and the resin. According to some embodiments, step (d) further comprises discarding the separated excess of said protected monomeric organic molecule.

According to some embodiments, step (d) comprises washing excess of said protected monomeric organic molecule thereby separating the excess of said protected monomeric organic molecule from the coupling product of the protected monomeric organic molecule and the resin in the reaction chamber. According to some embodiments, step (d) comprises washing excess of said protected monomeric organic molecule thereby separating the excess of said protected monomeric organic molecule from the coupling product of the protected monomeric organic molecule and the resin, such that the coupling product is remained in the reaction chamber.

According to some embodiments, both steps (c) and (e) are performed for a period of time, at a rotational rate of at least 600 rounds per minute, while maintaining a sheer rate of at least $3 \cdot 10^3$ sec$^{-1}$.

According to some embodiments, steps (c) to (e) are repeated at least 2, at least 3, at least 4, at least 5 or at least 7 cycles.

According to some embodiments, the method further comprises a step of cleaving the coupling product of step (e) from the resin thereby forming the polymeric organic molecule, thereby completing the solid phase synthesis thereof.

According to some embodiments, the method further comprises a step of isolating the polymeric organic molecule from the reaction mixture.

It is to be understood that the term "monomeric organic molecule" refers to any organic molecule, which upon sequential or cyclical coupling to other organic molecules (e.g. in solid phase syntheses) will form a corresponding polymeric organic molecule. Typically, monomeric organic molecules in SPS may include natural or synthetic building blocks, such as amino acids, nucleotides, nucleosides and monosaccharides or their derivatives or analogs. However, the term "monomeric organic molecule", as used herein further includes dimers, trimers and the like, which may act as building blocks in SPS. Thus, the methods provided herein include, for example, solid phase syntheses, where a resin bound to a monomeric amino acid is first coupled to a dipeptide, thereafter coupled to a tripeptide and then cleaved to form a hexapeptide.

According to some embodiments, the monomeric organic molecule is selected from the group consisting of an amino acid, a peptide, a saccharide, a nucleotide and a nucleoside. Thus the protected monomeric organic molecule is selected from the group consisting of an N-protected amino acid, an N-protected peptide, an O-protected saccharide, an O-protected nucleotide and an O-protected nucleoside. According to some embodiments, the monomeric organic molecule is selected from the group consisting of an amino acid, a monosaccharide, and a nucleoside. According to some embodiments, the monomeric organic molecule is an amino acid.

Thus, it is further to be understood that the term "polymeric organic molecule" refers to any organic molecule, which may be formed upon sequential or cyclical coupling to monomeric organic molecules (e.g. in solid phase syntheses). The nature of the polymeric organic molecule is dependent upon the identities of the monomeric organic molecules. Typically, polymeric organic molecules prepared in SPS may include natural/biological compounds, such as (poly)peptides, polynucleotides and polysaccharides.

The term "cycle" as used herein refers to a sequence of steps, which may be repeated for a plurality of times. These steps are collectively referred to as a single cycle. Thus, "cyclical" refers to a method, which at least some of its steps repeat in a cyclical manner.

The term "plurality" as used herein refers to an integer, which is equal or higher than two.

According to some embodiments the at least one step of the solid phase synthesis is coupling of a monomer to one of: the polymeric resin; an oligomeric chain attached to the polymeric resin; and an additional monomer attached to the polymeric resin; wherein the monomer and additional monomer are each independently selected from a saccharide, an amino acid and a nucleoside; and wherein the oligomer comprises at least one of a saccharide, an amino acid, a nucleotide and a nucleoside. According to some embodiments the saccharide is a monosaccharide.

According to some embodiments the at least one step of the solid phase synthesis is coupling of an amino acid to the polymeric resin or to an amino acid or peptide chain attached to the polymeric resin.

According to some embodiments the at least one step of the solid phase synthesis is coupling of a nucleoside to one of: the polymeric resin; a polynucleotide chain attached to the polymeric resin; a nucleoside attached to the polymeric resin; and a nucleotide attached to the polymeric resin.

According to some embodiments the at least one step of the solid phase synthesis is coupling of a saccharide to one of the polymeric resin; a polysaccharide chain attached to the polymeric resin; and a monosaccharide attached to the polymeric resin. According to some embodiments the saccharide coupled in the step is a monosaccharide.

According to some embodiments the at least one step of the solid phase synthesis comprises removal of a protecting group.

According to some embodiments the at least one step of the solid phase synthesis is selected from coupling of an amino acid to the resin, coupling of a nucleoside to the resin, coupling of a saccharide and removal of a protecting group. Each possibility represent a separate embodiment of the invention.

According to some embodiments the at least one step of the solid phase synthesis is selected from coupling of an amino acid to the resin and removal of a protecting group.

According to some embodiments the method comprises at least two steps of coupling a monomer to the resin and at least two steps of removal of a protecting group, wherein the monomer is selected from a saccharide, an amino acid and a nucleoside.

According to some embodiments the method comprises at least two steps of coupling of an amino acid to the resin and at least two steps of removal of a protecting group.

According to some embodiments the method comprises at least two steps of coupling of a saccharide to the resin and at least two steps of removal of a protecting group.

According to some embodiments the method comprises at least two steps of coupling of a nucleoside to the resin and at least two steps of removal of a protecting group.

According to some embodiments the at least one step of the solid phase synthesis is cleaving the synthesized molecule from the solid resin.

The method of the present invention may be applied for synthesis of any organic molecule capable of being synthesized on a solid support.

According to some embodiments, the organic molecule synthesis includes multiple steps.

According to some embodiments, the solid phase synthesis method is for synthesis of polymeric organic molecule selected from the group consisting of: peptide, polypeptide, modified peptide, peptidomimetic, oligonucleotide, peptide nucleic acid molecule and oligosaccharide. Each possibility represents a separate embodiment of the invention.

As used herein, the term "polymeric organic molecule" refers to any molecule comprised of linked monomer units, as long as the molecule includes at least two chemically linked monomer units. The term "polymeric molecule" is intended to be inclusive of short oligomers, such as, but not limited to dimers, trimers and tetramers, as well as oligomers of about maximum 50 monomers and of long polymers including up to about one hundred monomer units. According to some embodiments the polymeric organic molecule comprises 2-50, 2-30, 3-25 or 3-25 monomeric units. Preferably, the polymeric molecule is a biological polymer, in particular a polynucleotide, polysaccharide, polypeptide or an hybrid thereof. Hybrid molecules according to the invention include but are not limited to peptide-nucleic acid molecules (PNAs), glycoproteins and proteoglycans.

As used herein, the terms "polypeptide" and "oligopeptide" are well-known in the art, and are used to refer to a series of linked amino acid molecules. The term are intended to include both short peptide sequences, such as, but not limited to a tripeptide, and longer protein sequences. Similarly, the term "polynucleotide" or "oligonucleotide" refers to short or long oligomers of linked nucleotides, and the term "polysaccharide" refers to short or long oligomers of linked saccharide units. The term "hybrid" as used herein refers to oligomers and polymers having at least two types of monomers. For example, hybrid oligomers may include both saccharide(s), amino acid(s) nucleotide(s) and/or nucleoside(s) as building block monomers.

In other embodiments, the solid phase synthesis method is for synthesis of a peptide, polypeptide, modified peptide or peptidomimetic.

According to some embodiments, the method of the present invention is used for synthesis of combinatorial libraries or arrays. According to some embodiments, combinatorial libraries or arrays of peptides are created using the methods of the present invention.

As used herein the term "amino acid" refers to an organic acid containing both a protected or unprotected amino group (NHPG or $NH_2$) and an acidic carboxyl group (COOH). Typically, amino acids include α-amino acids. These include, but are not limited to, the 25 amino acids that have been established as protein constituents Amino acids contain at least one carboxyl group and one primary or secondary amino group on the amino acid molecule Amino acids include such proteinogenic amino acids as alanine, valine, leucine, isoleucine, norleucine, proline, hydroxyproline, phenylalanine, tryptophan, methionine, glycine, serine, threonine, cysteine, cystine, tyrosine, asparagine, glutamine, aspartic acid, glutamic acid, lysine, hydroxylysine, ornithine, arginine, histidine, penicillamine and the like. The term "amino acid" is intended to include both unprotected amino acids and protected amino acids.

According to some embodiments, the amino acid comprises a protected amino acid. According to some embodiments, the amino acid comprises an N-protected amino acid.

The term "N-protected amino acid" as used herein refers to an amino acid in which the amino group ($NH_2$) is protected by an amino-protecting group and is thus protected from taking part in chemical reactions that can occur during the coupling reaction(s). As the most abundant amino acids in various fields of biology and medicine are α-amino acids, N-protected amino acids typically comprise amino-protecting groups covalently attached to the α-amines. However, the current invention further encompasses solid phase syntheses, which employ less frequently used building blocks, such as ß-amino acids, where the amino group is separated from the carboxyl group by two carbon atoms. Thus, N-protected amino acids further comprise ß-amino acids, where amino-protecting groups are covalently attached to the ß-amines. According to some embodiments, the N-protected amino acid is selected from α-N-protected amino acid and ß-N-protected amino acid. According to some embodiments, the N-protected amino acid is α-N-protected amino acid. It is to be understood that "α-N-protected amino acids" and "ß-N-protected amino acids" respectively refer to α-amino acids comprising amino-protecting groups covalently attached to their α-nitrogen atom; and ß-amino acids comprising amino-protecting groups covalently attached to their ß-nitrogen atom.

The term "amino-protecting group" as used herein refers to a protecting group that preserves an amino group or an amino acid that otherwise would be modified by a chemical reaction in which an amino-containing compound (e.g. amino acid) is involved. Non-limiting examples of such protecting groups include the formyl group or lower alkanoyl group having from 2 to 4 carbon atoms, e.g., the acetyl or propionyl group; the trityl or substituted trityl groups, e.g., the monomethoxytrityl and dimethoxytrityl groups, such as 4,4'-dimethoxytrityl; the trichloroacetyl group; the trifluoroacetyl group; the silyl group; the phthalyl group; the (9-fluorenylmethoxycarbonyl) or "FMOC" group; the alkoxycarbonyl group, e.g., tertiary butoxy carbonyl (BOC); or other protecting groups derived from halocarbonates, such as, C6-Cn aryl lower alkyl carbonates. In the preparation of polypeptides in solid phase synthesis techniques, the FMOC group is typically employed.

As used herein the term "nucleoside" refers to a compound composed of any pentose or modified pentose moiety attached to a specific portion of a heterocyclic base, tautomer, or derivative thereof, such as the 9-position of a purine, 1-position of a pyrimidine, or an equivalent position of a heterocyclic base derivative. Nucleosides may include a phosphorus unreactive or reactive substituent, such as phosphoramidite. Examples include, but are not limited to, a ribonucleoside comprising a ribose moiety and a deoxyribonucleoside comprising a deoxyribose moiety, each may be possibly substituted with a phosphorus-containing substituent, such as phosphoramidite. According to some embodiments, the nucleoside can be a nucleoside drug analog. Examples of ribonucleosides include, but are not limited to, adenosine, guanosine, 5-methyluridine, uridine, 5-methylcytidine, cytidine, inosine, xanthosine and wybutosine, each may be possibly substituted with a phosphorus-containing substituent. Examples of deoxyribonucleoside include, but are not limited to, deoxyadenosine, deoxyguanosine, thymidine, deoxyuridine, deoxycytidine, deoxyinosine and deoxyxanthosine, each may be substituted with a phosphorus-containing substituent. The term "nucleoside" is intended to include both unprotected nucleosides and protected nucleosides.

As used herein, the term "nucleotide" refers to a nucleoside having a phosphate ester substituted on the 5'-position or an equivalent position of a nucleoside derivative. In cases where a phosphate analogue, such as phosphoramidite is present as a substituent, the molecule is customarily referred to as nucleoside rather than nucleotide. Nevertheless, in polynucleotide synthesis nucleoside building blocks having phosphorus groups (e.g. phosphoramidite) may ultimately be transformed to the corresponding phosphates, which leads to a change in terminology from nucleoside to nucleotide upon the reaction. Thus, when discussing chemical transformation and sequences herein, both "nucleotide" and "nucleoside" should be interpreted broadly to include phosphorus derivatives of nucleosides.

According to some embodiments, the nucleoside comprises a protected nucleoside. According to some embodiments, the nucleoside comprises an O-protected nucleoside. According to some embodiments, the nucleoside comprises a 5'-O-protected nucleoside.

The term "O-protected nucleoside" as used herein refers to a nucleoside in which at least one of its hydroxyl groups (OH) is protected by an oxygen-protecting group and is thus protected from taking part in chemical reactions that can occur during the coupling reaction(s). Thus, the term "5'-O-protected nucleoside" refers to a ribonucleoside or deoxyribonucleoside in which its 5' hydroxyl group is protected by an oxygen-protecting group. According to some embodiments the nucleoside is a ribonucleoside, which comprises oxygen-protecting groups on its 5' hydroxyl and on its 2' hydroxyl. According to some embodiments the nucleoside is a deoxyribonucleoside, which comprises an oxygen-protecting group on its 5' hydroxyl.

The term "oxygen-protecting group" as used herein refers to a protecting group that preserves an oxygen atom or an hydroxyl group that otherwise would be modified by a chemical reaction in which an oxygen-containing compound (e.g. nucleoside or saccharide) is involved. Non-limiting examples of such protecting groups include the trityl or substituted trityl groups, e.g., the monomethoxytrityl and dimethoxytrityl (DMT) groups, such as 4,4'-dimethoxytrityl; silyl ethers, such as trimethylsilyl and tert-butyldimethylsilyl; esters, such as acetate and halogenated acetates; lower alkyl groups, which may be substituted by a halogen atom or a cyano group; a benzyl group which may have a substituent; and a phenyl group which may have a substituent. In the preparation of polypeptides in solid phase synthesis techniques, trityl derivatives, in particular DMT are customarily employed.

As used herein the terms "sugar" and "saccharide" are interchangeable and refer to a compound comprising one or more monosaccharide groups. The term "monosaccharide" as used herein refers to the most basic units of carbohydrates. Monosaccharide are fundamental units of carbohydrates, which cannot be further hydrolyzed to simpler compounds. They are the simplest form of sugar and are usually colorless, water-soluble, and crystalline solids. Some monosaccharides have a sweet taste. Examples of monosaccharides include glucose, fructose and ribose. Monosaccharides are the building blocks of disaccharides (such as sucrose and lactose) and polysaccharides (such as cellulose and starch). With few exceptions (e.g., deoxyribose), monosaccharide have the chemical formula: $C_x(H_2O)_y$, where conventionally x≥3. Monosaccharides can be classified by the number x of carbon atoms they contain: triose (3) tetrose (4), pentose (5), hexose (6), heptose (7), and so on. In aqueous solutions monosaccharides exist as rings if they have more than four carbons. According to some embodiments, the saccharide(s) are monosaccharide(s). According to some embodiments, preferred monosaccharides are pentoses and/or hexoses.

According to some embodiments, the monosaccharide comprises a protected monosaccharide. According to some embodiments, the monosaccharide comprises an O-protected monosaccharide.

The term "O-protected monosaccharide" as used herein refers to a monosaccharide in which one of its hydroxyl groups (OH) is protected by an oxygen-protecting group and is thus protected from taking part in chemical reactions that can occur during the coupling reaction(s). According to some embodiments the monosaccharide is selected from pentose and hexose. According to some embodiments the monosaccharide is a pentose. According to some embodiments the monosaccharide is a hexose. According to some embodiments the monosaccharide comprises a single free hydroxyl, wherein its remaining hydroxyl(s) comprise protecting group(s). According to some embodiments the monosaccharide is a hexose comprising four O-protected hydroxyl groups and one free hydroxyl group. According to some embodiments the monosaccharide is a pentose comprising three O-protected hydroxyl groups and one free hydroxyl group.

The term "free" hydroxyl group, as used herein, refers to the unprotected OH chemical moiety. Similarly, the term "free" amine group, as used herein, refers to the unprotected $NH_2$ chemical moiety. Typically, "free" hydroxyl and/or amine groups are reactable in reactions, such as coupling reactions, whereas the corresponding protected groups would not undergo similar chemical reaction under similar conditions. According to some embodiments the method is for solid phase synthesis of an organic molecule comprising a total of 2-50, 2-20, 3-15, 3-10 or 3-6 residues selected from amino acid residues, nucleotide residues and saccharide residues. According to some embodiments the peptide comprises 2-50, 2-20, 3-15, 3-10 or 3-6 amino acid residues. According to some embodiments the polysaccharide comprises 2-50, 2-20, 3-15, 3-10 or 3-6 monosaccharide residues. According to some embodiments the polynucleotide comprises 2-50, 2-20, 3-15, 3-10 or 3-6 nucleoside residues.

As used here in the terms "coupling", "coupling process" or "coupling step" refer to a process of forming a bond between two or more molecules such as a two monomer units. A bond can be a covalent bond such as a peptide bond, a glycosidic bond or a phosphodiester bond.

A peptide bond is a chemical bond formed between two molecules when the carboxyl group of one coupling molecule reacts with the amino group of the other coupling molecule, thereby releasing a molecule of water ($H_2O$). This is a dehydration synthesis reaction (also known as a condensation reaction), and usually occurs between amino acids. The resulting —C(=O)NH— bond is called a peptide bond, and the resulting molecule is an amide.

A glycosidic bond is a chemical covalent bond formed between the hemiacetal or hemiketal group of a saccharide and the hydroxyl group of a second compound such as a second saccharide. Glycosidic bonds may be designated α- or β-based on the relative stereochemistry (R or S) of the anomeric position (i.e. C1 of the saccharide). Typically, polysaccharides are formed through formations of glycosidic bond between C1 of a first saccharide and an oxygen atom derived from a hydroxyl group of a second saccharide.

Phosphodiester bond refers to the covalent phosphate linkage between residues in a polynucleotide chain. It occurs when two of the oxygen atoms in phosphoric acid form two ester bonds. Phosphodiester bonds make up the backbone of the strands of nucleic acids. In DNA and RNA, the phosphodiester bond is the linkage between the 3' carbon atom of one sugar molecule and the 5' carbon atom of another, deoxyribose in DNA and ribose in RNA.

The terms "deprotection" and deprotecting as used herein refers to the removal of at least one protecting group. For example, deprotection comprises the removal of an amino-protecting group from a protected amino acid. More specifically, deprotection comprises replacing the FMOC protecting group attached to the amino group of a protected amino acid with a hydrogen atom, thereby forming a basic $NH_2$ group in a deprotected amino acid, according to some embodiments. Alternatively, when protecting groups are applied on oxygen atoms, deprotection comprises replacing the protecting group attached to the oxygen of a protected nucleoside with a hydrogen atom, thereby forming a free OH group in a deprotected nucleoside. The deprotection may be of one or a plurality of protecting groups. For a compound having n protecting groups, deprotecting will lead to the same compound having at least one less protecting group, i.e. the product compound will include between n−1 and 0 protecting groups.

The term "deprotected" refers to a compound, which underwent a removal of at least one protecting group. The term includes both compounds, which underwent removal of all of their protecting groups and compounds, which underwent removal of part of their protecting groups. For example, amino acids, such as lysine, arginine, aspartic acid, histidine, glutamic acid, serine, threonine, cysteine, tyrosine and the like, may include two protecting groups, a first protecting group covalently attached to the α-nitrogen and the second protecting group covalently attached to the reactive group of the side chain. In such cases, the deprotected amino acid may be defined as the amino acid after removal of only one protecting group or after removal of both protecting groups.

The term "unprotected" refers to a compound, which underwent a removal of all of its protecting group, or did not include protecting groups from the beginning. In other words, unprotected compound do not include protecting groups.

According to some embodiments, the method comprises the step of inserting at least two reactants into the reaction chamber.

According to some embodiments said at least one reactant is selected from the group consisting of: a deprotection agent, a coupling agent, a saccharide, a nucleoside and an amino acid. Each possibility represents a separate embodiment of the invention.

According to some embodiments said at least one reactant is selected from the group consisting of: a deprotection agent, a coupling agent and an amino acid.

According to some embodiments said N-protected amino acid is an α-N-protected amino acid. According to some embodiments said N-protected amino acid comprises a protecting group covalently attached to its α-nitrogen. According to some embodiments said N-protected amino acid comprises a protecting group selected from an Fmoc protecting group and a tBoc protecting group. According to some embodiments said protecting group is selected from an Fmoc protecting group and a tBoc.

According to some embodiments said N-protected amino acid is an Fmoc protected amino acid. According to some embodiments said protecting group is Fmoc protecting group. According to some embodiments said N-protected amino acid comprises a Fmoc group covalently attached to its α-nitrogen According to some embodiments said at least one reactant further comprises a reagent capable of removal of an Fmoc group.

According to some embodiments said reagent capable of removal of an Fmoc group comprises a base.

According to some embodiments said base comprises an amine.

According to some embodiments said amine is selected from the group consisting of piperidine, morpholine, piperazine, dicyclohexylamine, N,N-diisopropylethylamine, 4-dimethylaminopyridme, 1,8-diazabicycloundec-7-ene, pyrrolidme, cyclohexylamine, ethanolamine, diethylamme, trimethylamine, ammonia, tributylamine, 1,4-Diazabicyclo [2.2.2]octane, hydroxylamine, tris(2-aminoethyl)amine and combinations thereof.

According to some embodiments said O-protected nucleoside comprises a protecting group selected from benzyl, diphenylmethyl, trityl and derivatives thereof. Each possibility represent a separate embodiment of the invention. According to some embodiments said O-protected nucleoside is a dimethyltrityl (DMT) protected nucleoside. According to some embodiments said O-protected nucleoside is a 5' dimethyltrityl (DMT) protected nucleoside.

According to some embodiments said at least one reactant further comprises a reagent capable of removal of an DMT group. Reagents capable of removal of an DMT group are generally acidic compounds, such as but not limited to dicholoacetic acid and/or trichloroacetic acid According to some embodiments said O-protected monosaccharide comprises at least one protecting group selected from silyl ether, ester, benzyl, diphenylmethyl, trityl and acetal, each may be substituted by one or more halogen, cyano and/or nitro groups. Each possibility represent a separate embodiment of the invention.

According to some embodiments said period of time is in the range of 1-600, 10-300, 15-210, 5-60, 10-30, 30-180 or 60-120 minutes.

According to some embodiments said reactants further comprise a coupling reagent. Specifically, carbodiimides are considered to be useful coupling reagents in the formation of amide bonds (e.g. peptide bonds), whereas various azole compounds are useful catalysts in formations of P—O bonds (e.g. phosphodiester bonds); and various reagents promote formations of glycosidic bonds depending on the polysaccharide structure to be formed.

According to some embodiments said coupling reagent comprises a carbodiimide.

According to some embodiments said inserting of at least one reactant to the reaction chamber comprises gradually inserting of at least one reactant to the reaction chamber. According to some embodiments the inserting of the carbodiimide to the reaction chamber comprises gradually inserting of the carbodiimide to the reaction chamber.

According to some embodiments said carbodiimide is selected from the group consisting of 1-ethyl-3-(3-dimethylaminopropyl)carbodiimide, N,N'-dicyclohexylcarbodiimide, N,N'-Diisopropylcarbodiimide and combinations thereof.

According to some embodiments said carbodiimide comprises ethyl-3-(3-dimethylaminopropyl)carbodiimide.

According to some embodiments said reactants further comprise 1-hydroxybenzotriazole (HOBt).

According to some embodiments said coupling reagent comprises an azole catalyst. According to some embodiments said azole catalyst is selected from the group consisting of 1H-tetrazole, 2-ethylthiotetrazole, 2-benzylthiotetrazole, 4,5-dicyanoimidazole and combinations thereof.

According to some embodiments the method further comprises inserting at least one solvent into the reactor.

The term "solvent" as used herein refers to a fluid media, particularly liquid media, in which chemical transformation occur. The term is used broadly to include both liquid media, which dissolves the reactants involved in said transformation and media in which some of said reactants are insoluble. Thus, it is to be understood that in solid phase syntheses as described herein the reactant(s) may be soluble in the solvent, whereas the functionalized polymeric resin may be insoluble.

According to some embodiments the at least one solvent is selected the group consisting of from water, dimethylformamide, dichloromethane, N-methyl-2-pyrrolidone, dimethylacetamide and combinations thereof.

According to some embodiments said solvent comprises N-methyl-2-pyrrolidone.

According to some embodiments said solvent comprises water.

According to some embodiments said solvent comprises N-methyl-2-pyrrolidone and water.

According to some embodiments the method comprises an initial step of swelling said beads of polymeric resin in a solvent. According to some embodiments the step of swelling is performed after the step of inserting the beads and the solvent into the reactor; and prior to the step of inserting the reactant to the reaction chamber.

According to some embodiments the polymeric resin is in a concentration of 5-25% w/w, 5-20% w/w, 5-15% w/w or 8-12% w/w in the solvent.

According to some embodiments said swelling step comprises mixing said beads of polymeric resin for a specified period of time in said solvent. According to some embodiments said period of time is in the range of 1-60, 2-45 or 4-30 minutes.

According to some embodiments said rotational rate is in the range of 600-1400 rpm. According to some embodiments said rotational rate is in the range of 600-1200 rpm. According to some embodiments said rotational rate is in the range of 600-1000 rpm. According to some embodiments said rotational rate is in the range of 600-900 rpm. According to some embodiments said rotational rate is in the range of 600-800 rpm. According to some embodiments said rotational rate is in the range of 600-700 rpm.

In yet other embodiments, a rotational rate in the range of 5,000-30,000 is maintained using a homogenizer. According to some embodiments, a rotational rate in the range of 10,000-30,000 is maintained using a homogenizer.

According to some embodiments said mixing said beads of polymeric resin for a specified period of time in said solvent, comprises maintaining sheer rate of at least $3 \cdot 10^3$ $\sec^{-1}$.

In other embodiments, said mixing said beads of polymeric resin for a specified period of time in said solvent, comprises maintaining sheer rate of at least $1 \cdot 10^6$ $\sec^{-1}$.

According to some embodiments said mixing said beads of polymeric resin for a specified period of time in said solvent, comprises maintaining sheer stress of at least 1.5 $N/m^2$. According to some embodiments said sheer stress is in the range of 1.5-5, 1.8-3.8, 1.8-3.0 or 1.8-2.4 $N/m^2$.

In other embodiments, a shear stress of 500-2000 $N/m^2$ is maintained using a homogenizer. According to some embodiments, a shear stress of 750-1500, or 900-1200 $N/m^2$ is maintained using a homogenizer.

A functionalized polymeric resin according to the invention is any polymeric resin comprising a reactive group to which an organic molecule may be coupled.

A reactive group of a polymeric resin according to the invention includes but is not limited to, an amino group, hydroxyl group carboxy group, a carboxylic derivative group, such as acyl halide, halo group and pseudo-halo group, such as a sulfonate derivative.

According to some embodiments, the functionalized resin comprises a residue selected from an amino acid residue, a nucleotide residue, a nucleoside residue and a saccharide residue. According to some embodiments, the functionalized resin comprises an amino acid residue. According to some embodiments, the functionalized resin comprises a saccharide residue. According to some embodiments, the functionalized resin comprises a nucleotide residue.

According to some embodiments said functionalized beads of polymeric resin comprises polystyrene-divinylbenzene.

According to some embodiments said polystyrene-divinylbenzene comprising resin is selected from 1% DVB-PS chloromethylated resin and Rink Amide Tentagel resin.

According to some embodiments said resin is 1% DVB-PS-chloromethylated resin.

According to some embodiments said resin is Rink Amide Tentagel resin.

According to some embodiments said beads of polymeric resin comprise coupling capacity in the range of 0.2-0.6 mmol/g, 0.3-0.5 mmol/g or 0.35-0.45 mmol/g.

According to some embodiments said beads of polymeric resin have particle size in the range of 20-200, 50-100, 60-90, 65-85, 70-80 or 73-77 μm.

According to some embodiments said mechanical stirrer comprises at least three blades rotatable about an axis. According to some embodiments said mechanical stirrer comprises three blades rotatable about an axis. According to some embodiments said blades rotatable about an axis are spinning upwards at a first angle. According to some embodiments said first angle is in the range of 20-40°, 25-35° or 30-35°.

According to some embodiments said blades rotatable about an axis are spinning downwards at a second angle. According to some embodiments said second angle is in the range of 30-50°, 35-45° or 40-45°.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION OF THE INVENTION

Figure 2:
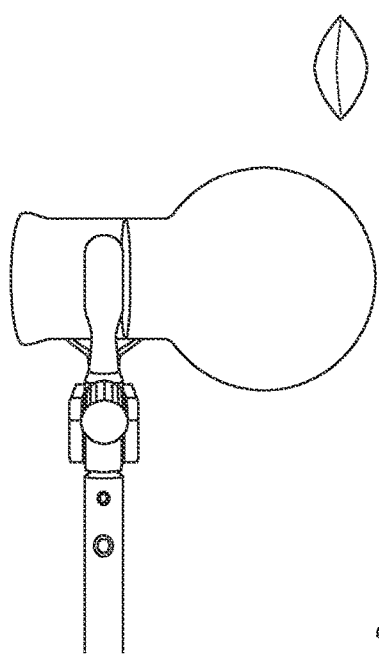
FIG. 2 is a photograph of a magnetic stirrer apparatus.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The methods of the present invention are suitable of synthesis of any organic molecule which can be synthesized on a solid support. This includes both polymeric molecules such as peptides and polynucleotides. The methods are particularly suitable for molecules produced using multiple synthesis steps and requiring orthogonal protection of reactive groups.

The methods of the present invention provide at least one improvement in synthesis parameters, including but not limited to synthesis time, synthesis yield, reduction of side product formation, and reduction of racemization rate.

Without wishing to be bound to any mechanism of action, these improvements may be due to applying high shear force during synthesis steps, elimination of accumulation of reactants or intermediates in the reaction mixture, and maintaining of reaction mixtures having improved homogeneity.

Some of the mixing apparatuses that may be employed according to the present invention were not previously used or disclosed for organic synthesis. These include for example homogenizers (rotor-stator and other type of homogenizers), that are commonly used in biology for distraction of tissues, for example.

A rotor-stator homogenizer employs a high speed, tightly fitted rotor inside a toothed stator. The samples to be homogenized are drawn into the center of the rotor having been mixed, accelerated and pressed through the narrow gap between the rotor and stator.

Basic understanding of hydrodynamic energies, as well as shear and compressive stress and forces applied to the reaction media could be critical to the success of scale up synthesis processes. Nevertheless, up till now very few investigation were made on the influence of the hydrodynamic parameters on the yield and side reactions in SPS. Some important hydrodynamic parameters include 'shear rate', 'shear stress', and 'shear force'.

The term 'shear rate', measured in inverse seconds (SI unit) refers to rate at which a progressive shearing deformation is applied to a material. As used herein, shear rate refers to the rate at which the deformation is applied to the polymeric resin beads within the reaction mixture while being mixed. Generally, the shear rate for a fluid flowing between two parallel plates, one moving at a constant speed and the other one stationary is defined by:

$$\dot{\gamma} = v/h'$$

wherein γ is the shear rate; v is the velocity of the moving plate (in sec$^{-1}$); and h is the distance between the two parallel plates. For the simple shear case, it is just a gradient of velocity in a flowing material.

In stirred tanks, the following correlations were derived [Perez et al. Chem Eng. J. 124, 2006, 1; and Metzner and Otto AIChE Journal, 3, 1957, 3]:

$$\gamma = \frac{P}{\tau \cdot V} \quad \gamma = k_i N$$

wherein $k_i$ is an impeller constant; N is the agitation speed, (i.e. the rotational speed of the impeller) measured in sec$^{-1}$; τ is the shear stress measured in pascal (newton per square meter); P is the power input (in Watts), which depends on the torque of the impeller and on its rotational speed (N); and V is the volume of the fluid in the tank.

The term 'shear stress', measured in inverse seconds refers to a component of stress coplanar with a material cross section. As used herein, shear stress refers to the component of stress applied on the polymeric beads, which is coplanar with their cross section. Generally, shear stress arises from the force vector component parallel to the cross section.

Being a measure of stress, shear stress is measured in force per unit area (in SI units: N/m$^2$)

$$\tau = F/A'$$

wherein τ is the shear stress; F is the force applied; and A is the cross-sectional area of material with area parallel to the applied force vector (i.e. cross-sectional area of the beads).

With reference to other hydrodynamic parameters, shear stress can also be derived from shear rate by: $\tau = \dot{\gamma}\mu$ where μ is the dynamic viscosity of the fluid.

The term 'viscosity' refers to a hydrodynamic property of a fluid depicting its measure of resistance to gradual deformation by shear stress or tensile stress. Viscosity arises from collisions between neighboring particles in the fluid that are moving at different velocities. As used herein, viscosity refers to the viscosity of the reaction mixture comprising the solvent, the beads and other added reagents.

The term 'shear force' refers to a force acting in a direction parallel to a surface or to a planar cross section of a body. As used herein, shear force refers to the force acting in a direction parallel to a surface or to a planar cross section of the polymeric beads while being mixed. Shear force, Fs, can be derived from shear stress as it consists of the integrated shear stress (τ) over the surface area (A) of a body.

$$Fs = \int_A \tau dA$$

Being heterogeneous reactions, (i.e. where the protected amino acids are in solution, whereas the resin is not) the reactions performed in the SPS cycle are diffusion controlled reactions highly affected by stirring or agitation. As described above gentle mixing methods are routinely employed in the large scale production of peptides (e.g. vortex, nitrogen stream, rotary evaporator rotor, agitation by rocking), such that a low shear stress over the polymeric beads is maintained thereby avoiding damage thereof. In contrast with the gentle mixing approach in solid phase synthesis, mixing methods used in the production of small molecules in solution are frequently performed in high rpm.

The influence of the typically employed gentle mixing in SPS is not well documented and characterized. There are two main parameters that could be critical in the steps of the SPS cycle (i.e. coupling of protected building block; deprotection and washing). First, compressive and shear stress applied to the resin beads could cause them to break and as a consequence the isolation process will be tedious due to slow filtration and possible blockage of the filter. Second, the rates of the coupling and the deprotection reactions and the washing steps might be influenced by breaking up of the beads. Moreover, a secondary parameter stem from the interaction between the solid phase (resin beads) and the liquid phase. The better distribution of the resin beads, caused by circular flow rate of the beads in the media, could increase the mass transfer between the liquid bulk to the solid surface and thus accelerate the reaction. In specific reactions, it could decrease the generation of impurities and improve the impurity profile of the final product.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

Example 1—Resin Beads Stability Check

Equipment and Configuration

Figure 3:
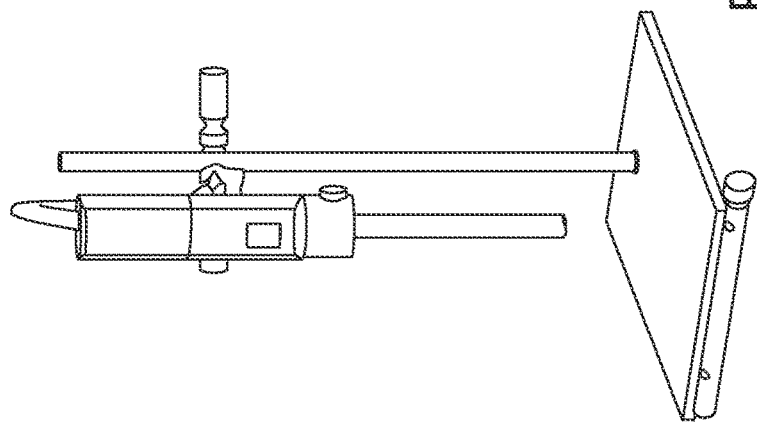
FIG. 3 is a photograph of a homogenizer stirrer apparatus (Apparatus 3).
Figure 1B:
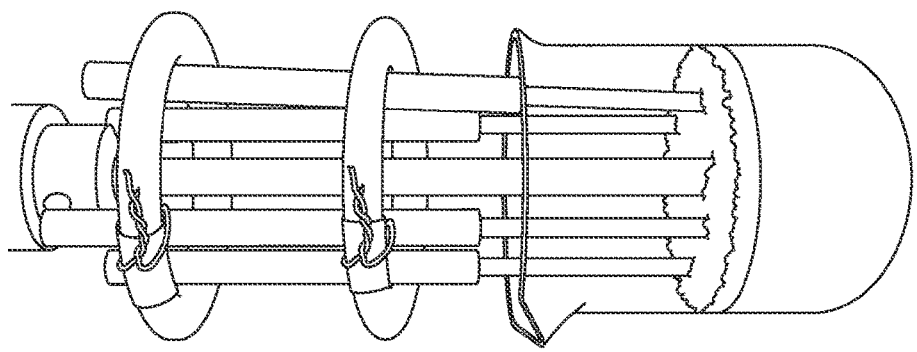
FIG. 1B is a close-up photograph of an HS-SPS apparatus according to some embodiments.
Figure 1A:
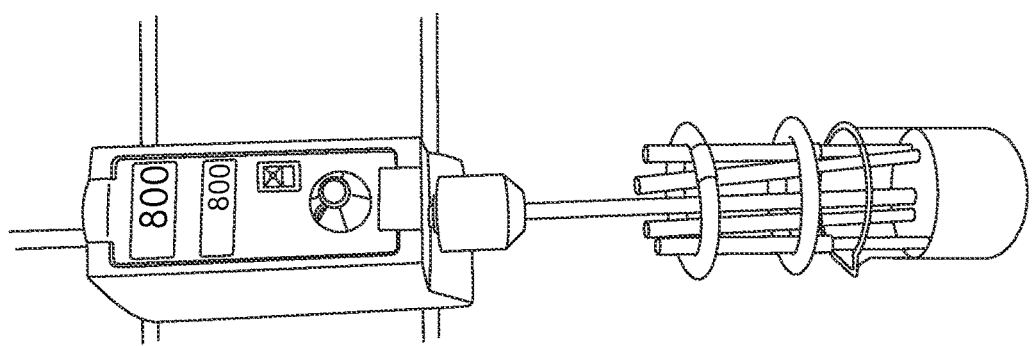
FIG. 1A is a photograph of an High Sheer SPS (HS-SPS) apparatus according to some embodiments.

In order to characterize and optimize the process for industrial application, the influence of the equipment operation and geometry, namely the hydrodynamics of the system, on the process was estimated. The study evaluated the stability of polymeric resin beads consequent to mixing, and compared three mixing methods:
  (i) A mixing method including an HS-SPS apparatus consistent with some embodiments of the invention (FIGS. 1A and 1B).
  (ii) A mixing method using a magnetic stirrer (FIG. 2).
  (iii) A mixing method using a homogenizer (FIG. 3).

The HS-SPS apparatus consisted of a reactor including a 250 mL beaker flask (6.8 cm diameter and 10 cm height) equipped with a mechanical stirrer and a high shear stress equipment. The reactor also included 4 baffles of 0.6 cm thickness each. Two mechanical stirrers were examined:
  1. A stirrer consisting of a small impeller with three 3.8 cm long blades spinning upwards at an angle of 32.2°. The apparatus comprising this stirrer is referred as the 'HS-SPS Apparatus 1' or 'Apparatus 1' hereinafter.
  2. A BOLA-mini impeller stirrer with three 5 cm long blades and impeller height of 35 cm, spinning downwards at an angle of 41.1°. The apparatus comprising this stirrer is referred as the 'HS-SPS Apparatus 2' or 'Apparatus 2' hereinafter.

This kind of equipment, in different configurations, is widely used in the fine chemical and Active Pharmaceutical Ingredient (API) industry at all volume levels, although similar apparatuses have been considered unfitting for processes employing solid phase synthesis in general and solid phase peptide synthesis in particular.

The magnetic stirrer apparatus consisted of a 250 ml round bottom flask and an oval or octagonal shaped magnetic stirrer. The magnetic stirrer's geometries:
  Length=25 mm;
  Width=10 mm;
  Perimeter=43 mm;
  Diameter=12 mm;
  Weight=6.6189 g;
  Distance between parallel stripes=5 mm.

The homogenizer apparatus of FIG. 3 (referred as the 'HS-SPS Apparatus 3' or 'Apparatus 3') consisted of a 250 mL beaker flask (6.8 cm diameter and 10 cm height) equipped with a Polytron PT 6100,PT-DA3020/ZEC homogenizer including geometries as follows:
  Homogenizer diameter=2 cm;
  Round window diameter=1 cm;
  Number of teeth=14;
  Number of windows=14;
  Height of window (from bottom)=0.3 cm;
  Width of window=0.2 cm
  Z(window)=0.8 cm Two types of PS-DVB (polystyrene-divinylbenzene) based resins were used: (i) a traditional PS-1% DVB (a polystyrene consisting of 1% divinylbenzene monomers) chloromethylated resin (Merrifield resin); (ii) Rink Amide Tentagel resin (a modified PS-1% DVB polymer grafted with ethylene oxide monomers, including a Rink Amide linker). Specifically, this resin was 'TentaGel HL RAM, 12 023' purchased from RAPP POLYMER having a capacity of 0.4 mmol/g and particle size of 75 μm.

Mechanical stabilities of the resins were tested in both directions. Shear stress was applied to a mixture of the two resins in N-Methylpyrrolidone (NMP) and water solvents, for different time periods. The concentration of beads in the solvents were set to 10% w/w, 12.5 g beads in 125 g of solvent.

The stability of the resin beads was checked under a high power microscope to reveal any damage. The microscope that was used to view and measure the beads is a Zeiss scope A.1 AxioCam iCc3 microscope.

Results

First, the HS-SPS Apparatus 1 was examined with water as solvent and the TentaGel resin. Spinning the impeller at 1450 rpm resulted in a turbid solution due to air entrance to the vessel. Only at about 600-700 rpm, the solution didn't appear turbid and no vortex was created so the maximal impeller rotation speed was set at that speed.

Figure 4C:
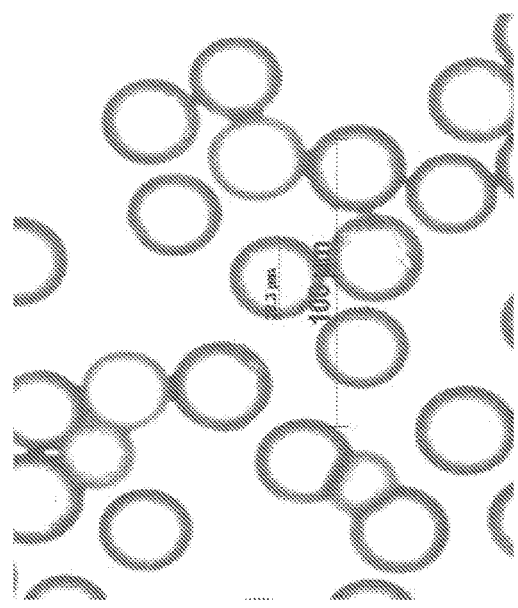
FIG. 4C is a photograph of TentaGel resin beads after 30 minutes of being rotated in water in HS-SPS Apparatus 1.
Figure 4B:
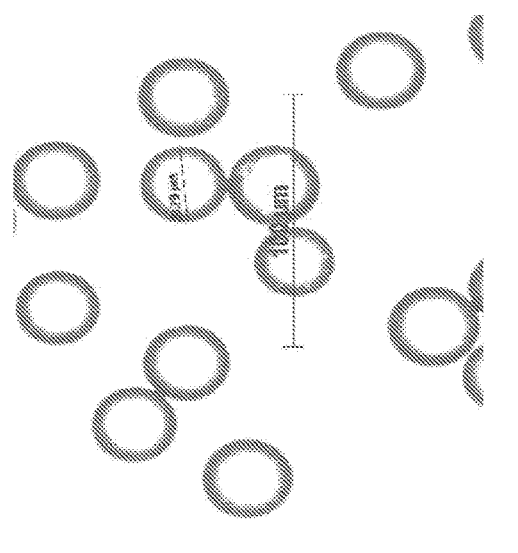
FIG. 4B is a close-up photograph of TentaGel resin beads after 30 minutes of being rotated in water in HS-SPS Apparatus 1.
Figure 4A:
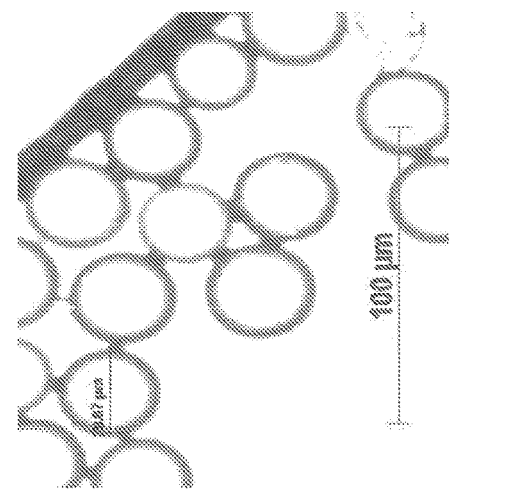
FIG. 4A is a photograph of TentaGel resin beads before being rotated in water in HS-SPS Apparatus 1—a stirrer consisting of a small impeller with three 3.8 cm long blades spinning upwards at an angle of 32.2°.
Figure 5C:
FIG. 5C is a photograph of TentaGel resin beads after 1.1 minutes of being rotated in water in HS-SPS Apparatus 1.
Figure 5B:
FIG. 5B is a photograph of TentaGel resin beads after 42 seconds of being rotated in water in HS-SPS Apparatus 1.
Figure 5A:
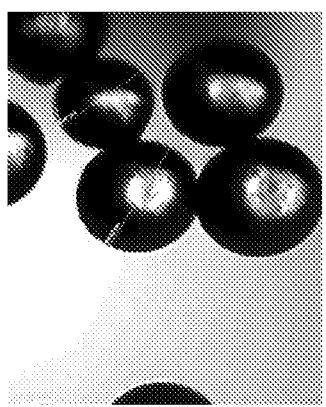
FIG. 5A is a photograph of TentaGel resin beads before being rotated in water in HS-SPS Apparatus 1.
Figure 5F:
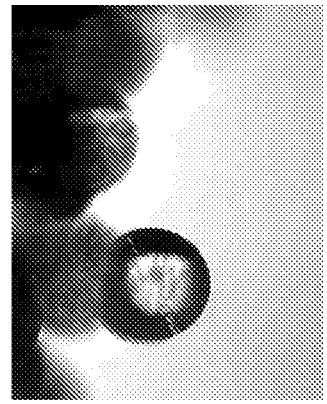
FIG. 5F is a photograph of TentaGel resin beads after four hours of being rotated in water in HS-SPS Apparatus 1.
Figure 5E:
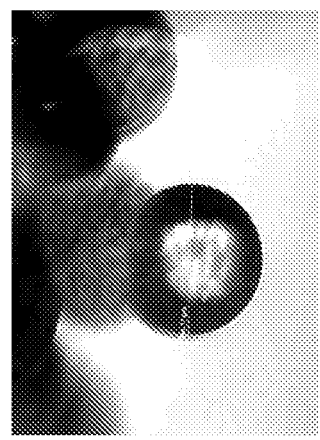
FIG. 5E is a photograph of TentaGel resin beads after three minutes of being rotated in water in HS-SPS Apparatus 1.
Figure 5D:
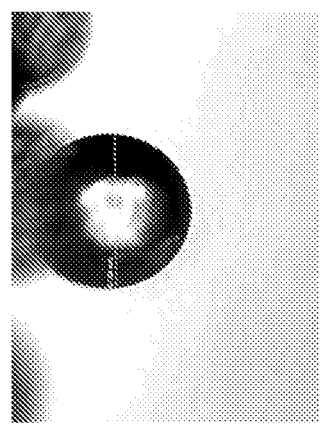
FIG. 5D is a photograph of TentaGel resin beads after two minutes of being rotated in water in HS-SPS Apparatus 1.

The beads were rotated in the mechanic stirrer of the HS-SPS Apparatus 1, in water for 24 hours at room temperature. Samples were taken every 30 minutes for the first 8 hours, and a final sample was taken after 24 hours. As can be seen in FIG. 4 the diameter of the beads remained substantially unchanged. Thus, in order to test the beads' swelling, the kinetics was tested under the microscope, without any stirring, at small time intervals.

As seen in FIGS. 5A-F, the beads remained in a flawless round shape, before and after being stirred for 24 hours in the HS-SPS Apparatus 1. Moreover, the swelling of the beads took place as expected (Table 1).

TABLE 1

Swelling of TentaGel beads in water hours in HS-SPS Apparatus 1

| Time (min) | Beads' average diameter (μm) |
| --- | --- |
| 0 | 95.45 |
| 42 sec | 102.12 |
| 1.1 | 106.74 |
| 2 | 107.08 |
| 3 | 106.77 |
| 4 | 107.74 |

In the next stage of the experiment, after the stirring of the beads in water for 24 hours, their durability towards stirring under high shear stress was tested in the homogenizer apparatus. In the experiment, half of the initial solution used in the HS-SPS Apparatus 1 experiment was stirred for five more minutes at 23,000 rpm in the homogenizer apparatus, resulting in only few of the beads damaged in shape.

Next, the durability of the beads, which were stirred by the HS-SPS Apparatus 1 and the homogenizer apparatus, was examined using the magnetic stirrer apparatus. After 24 hours and after one week of stirring, a sample was taken and observed under the microscope.

The procedure above conducted with TentaGel beads in water with HS-SPS Apparatus 1, was repeated with TentaGel beads in NMP with HS-SPS Apparatus 2; and with polystyrene beads in NMP HS-SPS Apparatus 2 (polystyrene in water is irrelevant, due to this polymer poor swelling in aqueous conditions). In all cases, the shear stress was measured using a dynamometer (Dynamometer FH 10 from PCE instruments). Table 2 summarizes the stabilities of the different beads corresponding to the stirring time, the apparatus and stresses employed.

applying the same kind of shear stress. However, because the magnetic bar agitator is located at the bottom of the flask, significant amounts of compressive stress are also applied. The direction of the stress tension may be the main reason for the destruction of the resin in magnetic stirred vessels.

Example 2—Resin Beads Swelling Examination

Swelling of the dry resin beads is performed in the initial stages of solid phase peptide synthesis processes. NMP, DMF (dimethylformamide) and DCM (dichloromethane) are considered good swelling solvents for polystyrene-divinylbenzene based resins and are routinely used in SPSS processes, although TentaGel resins are known to also swell to some extent in water. The swelling is a direct function of the interaction and compatibility of the solvent properties with the resin and the operation conditions in the equipment.

TABLE 2

Sensitivity of various resins toward shear stress and operation rate.

|  | Stability | | | | | |
|---|---|---|---|---|---|---|
|  | Mechanical Stirrer | | Magnetic Stirrer | | Homogenizer | |
|  | Water[1] | NMP[2] | Water | NMP | Water | NMP |
| TentaGel | 24 h Stable | Stable above 24 h | Not stable After 2-3 Days | After 2 hour not stable | 15 min Stable | 5 min Stable |
| Merrifield resin | Not relevant* | 1 week Stable | Not relevant* | After 2 hour no stable | Not relevant* | 5 min Stable. |
| Compressive stress | Not relevant* | Not relevant* | 15.6 N/m$^2$ | 21.1 N/m$^2$ | Not relevant* | Not relevant* |
| Shear stress | 1.84 N/m$^2$ | 2.4 N/m$^2$ | 8 N/m$^2$ | 11 N/m$^2$ | 1540 N/m$^2$ | 2042 N/m$^2$ |

[1]With HS-SPS Apparatus 1;
[2]With HS-SPS Apparatus 2.

Figure 6A:
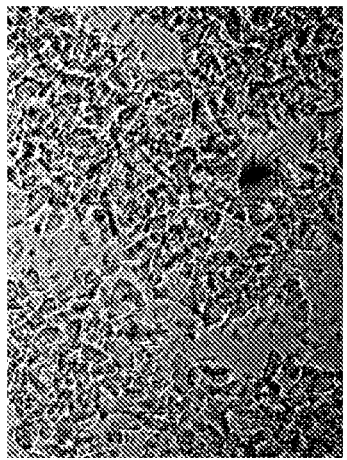
FIG. 6A is a photograph of TentaGel resin beads before being rotated in water in a magnetic stirrer.
Figure 6B:
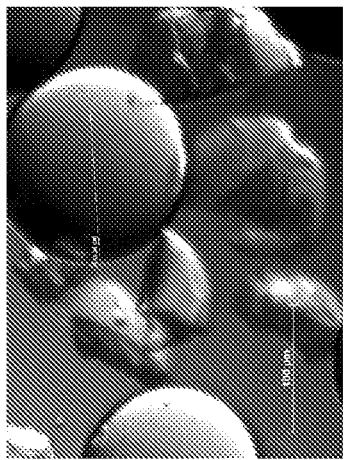
FIG. 6B is a photograph of TentaGel resin beads after two hours of being rotated in water in a magnetic stirrer.
Figure 6C:
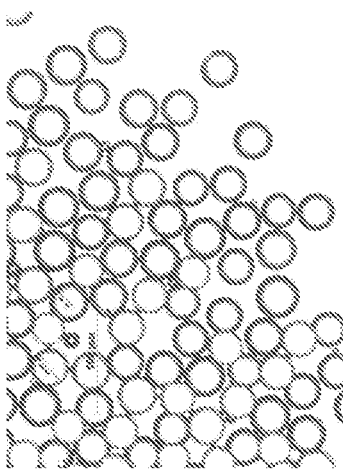
FIG. 6C is a photograph of TentaGel resin beads after 18 hours of being rotated in water in a magnetic stirrer.
Figure 7A:
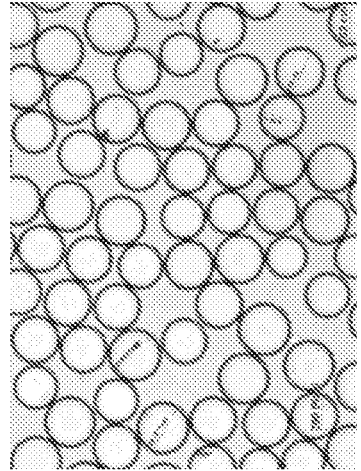
FIG. 7A is a photograph of TentaGel resin beads before being rotated in NMP in HS-SPS Apparatus 2—A BOLA-mini impeller stirrer with three 5 cm long blades (h=35 cm spinning downwards at an angle of 41.1°.
Figure 7B:
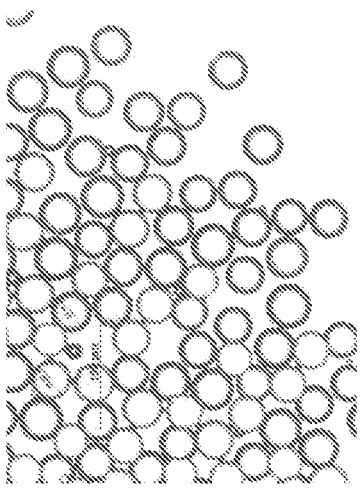
FIG. 7B is a photograph of TentaGel resin beads after 24 hours of being rotated in NMP in HS-SPS Apparatus 2.

Table 2 and FIGS. 7A-7B reveal that, surprisingly, even at high shear rate operations with the HS-SPS Apparatus or with the homogenizer apparatus, the resin beads were not damaged. The only configuration that damaged the resin beads was the employment of the magnetic stirrer apparatus. FIGS. 6A-C shows the structural difference of the resin before and after stirring in the magnetic stirrer apparatus. It is apparent that the beads are significantly damage in structure after 2 hours of stirring in the magnetic stirrer apparatus (FIG. 6B), whereas after 18 hours in the same conditions a complete smearing of the beads is observed, which practically led to their disappearance (FIG. 6C). Unexpectedly, these finding were in complete contrast to the results under similar conditions with HS-SPS Apparatus 1 and HS-SPS Apparatus 2. As shown in Table 2, both TentaGel beads and Merrifield resin beads remained stable over 24 hours of high shear rate stirring in the different solvents. For example, stirring Tentagel beads with NMP solvent in HS-SPS Apparatus 2, did not have visible effect on the structure of the beads, as can be inferred upon comparison of microscope inspections before (FIG. 7A) and after (FIG. 7B) stirring in the in HS-SPS Apparatus 2.

Without wishing to be bound by any theory or mechanism, the unexpected variance between magnetic and mechanical stirring stems from the different levels of compressive stress applied by each apparatus. The HS-SPS Apparatus is applying mainly shear stress to the media at different levels. Similarly, the magnetic stirring apparatus is In the frequently used shaker reaction vessels the swelling step is typically complete within one to two hours.

Swelling kinetic of the polymeric beads was tested in an agitated tank, by adding the beads to a solvent in the tank and stirring at 600-700 rpm for two hours. Much like in the stability evaluation experiments, swelling kinetics of TentaGel bead were evaluated in water with HS-SPS Apparatus 1, and in NMP solvent with HS-SPS Apparatus 2, whereas Merrifield resin beads bead were evaluated only in NMP with HS-SPS Apparatus 2.

Samples were taken every 30 seconds and examined under the microscope. For each sample, the mean diameter of the beads was measured by the microscope's software. Since the beads swelled at a short time in NMP it was decided to test also swelling without agitation under the microscope in small time intervals to observe the effect of the solvent itself in real time. A photograph was taken every 30 seconds for the first two minutes and then every minute for the remaining two minutes. This procedure was conducted for the same samples mentioned above. Diameter growing of the beads was measured under two types of operations at different times: (1) directly under the microscope by adding resin to a solvent film without agitation, and (2) in the mechanically stirred device with high shear stress equipment. The results are shown in Table 3.

TABLE 3

Swelling kinetics of two resins.

| Solvent | Water | | | | NMP | | | |
|---|---|---|---|---|---|---|---|---|
| Resin | No agitation | | With agitation | | No agitation | | With agitation | |
| Tentagel | 0 min | 105 μm | 1 min | 106 μm | 0.5 min | 150 μm | 1 min | |
| | 4 min | 107 μm | 10 min | | 4 min | 150 μm | 10 min | |
| | | | 30 min | 120 μm | | | 30 min | 300 μm |
| Merrifield resin | NR | | NR | | 0.5 min | 50 μm | 2 hour | 140 μm |
| | | | | | 2 hour | 90 μm | | |

NR—not relevant

Figure 8C:
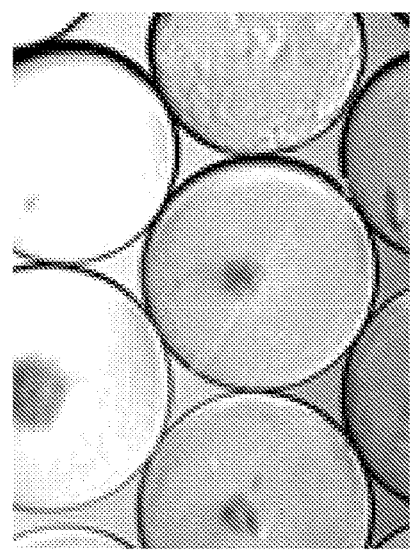
FIG. 8C is a photograph of TentaGel resin beads after 30 minutes of being rotated in NMP in HS-SPS Apparatus 2.
Figure 8B:
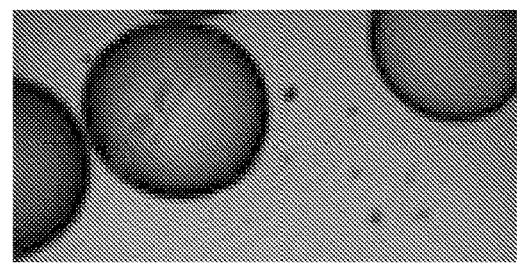
FIG. 8B is a photograph of TentaGel resin beads immediately after contact with NMP.
Figure 8A:
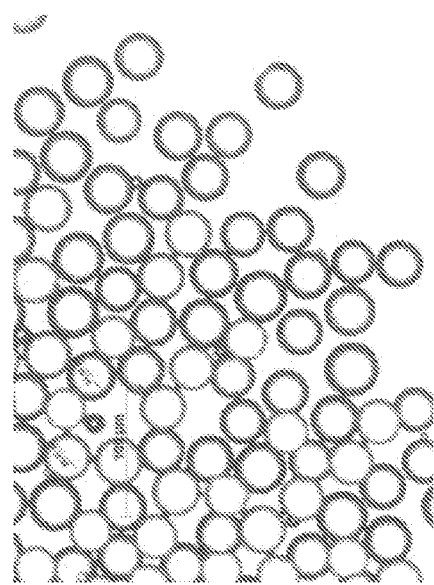
FIG. 8A is a photograph of TentaGel resin beads without solvent.
Figure 9D:
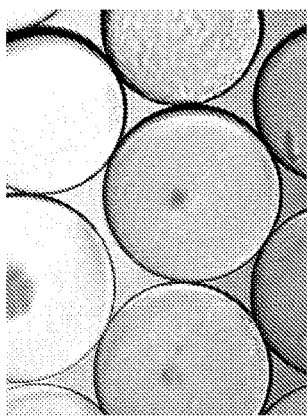
FIG. 9D is a photograph of TentaGel resin beads after 1.3 minutes of being rotated in NMP in HS-SPS Apparatus 2.
Figure 9H:
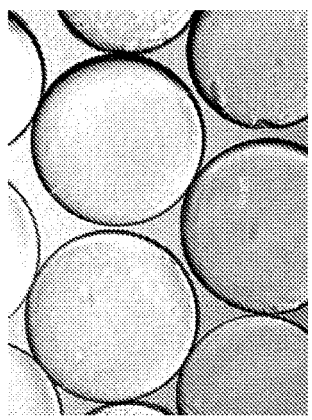
FIG. 9H is a photograph of TentaGel resin beads after four minutes of being rotated in NMP in HS-SPS Apparatus 2.
Figure 9C:
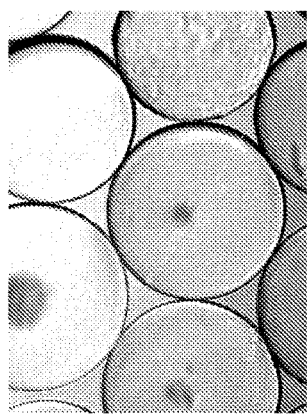
FIG. 9C is a photograph of TentaGel resin beads after one minute of being rotated in NMP in HS-SPS Apparatus 2.
Figure 9G:
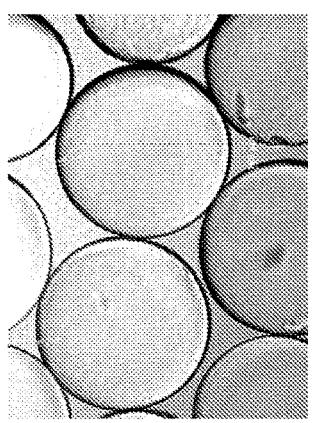
FIG. 9G is a photograph of TentaGel resin beads after three minutes of being rotated in NMP in HS-SPS Apparatus 2.
Figure 9B:
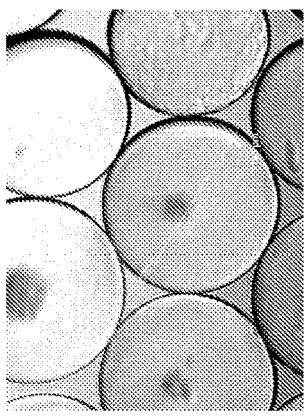
FIG. 9B is a photograph of TentaGel resin beads after 30 seconds of being rotated in NMP in HS-SPS Apparatus 2.
Figure 9F:
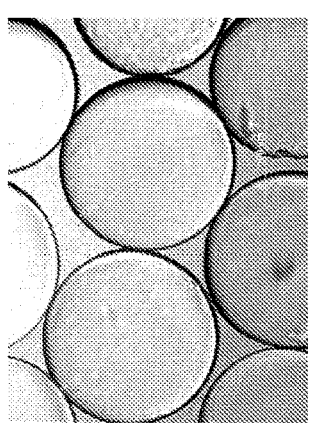
FIG. 9F is a photograph of TentaGel resin beads after 2.3 minutes of being rotated in NMP in HS-SPS Apparatus 2.
Figure 9A:
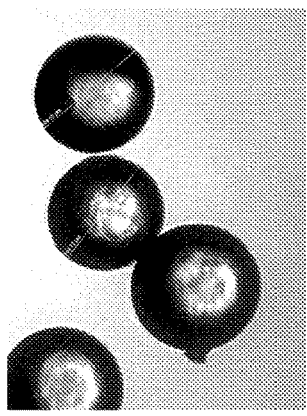
FIG. 9A is a photograph of TentaGel resin beads before being rotated in NMP in HS-SPS Apparatus 2.
Figure 9E:
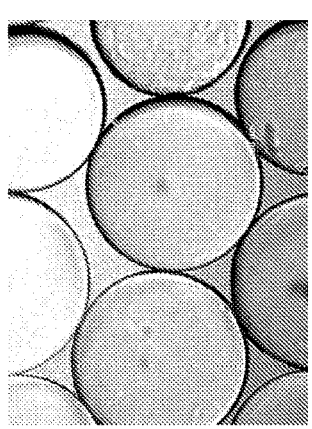
FIG. 9E is a photograph of TentaGel resin beads after two minutes of being rotated in NMP in HS-SPS Apparatus 2.

It was found that immediately upon contact of both two resins with NMP, they swells to about half of their maximal extent. When immersed in NMP, Tentagel swells to a diameter of about 150 μm within few seconds, whereas upon stirring in HS-SPS Apparatus 2, it swells to 300 μm diameter within 30 minutes. FIG. 8 shows the starting beads before contact with NMP (FIG. 8A); the same beads immediately after contact with NMP (FIG. 8B); and the beads after 30 minutes of mechanical stirring in NMP in HS-SPS Apparatus 2 (FIG. 8C). No damage to the resins was observed in this study as can be further concluded from FIGS. 9A-H. The beads' average diameter as function of time increased as expected (Table 4).

TABLE 4

Swelling of TenraGel resin in NMP with HS-SPS Apparatus.

| Time (min) | Beads' average diameter (μm) |
|---|---|
| 0 | 104.51 |
| 0.5 | 157.19 |
| 1 | 156.81 |
| 1.3 | 154.79 |
| 2 | 152.39 |
| 2.3 | 153.37 |
| 3 | 151.04 |
| 4 | 152.83 |
| 30 | 300 μm |

From the results above it is concluded that short time swelling can be employed to the resin, thereby reducing the total time of synthesis.

Example 3—Coupling and Racemization Examination

As mentioned, peptide synthesis is usually conducted in the solid phase by employing a shaker apparatus. In order to demonstrate the feasibility of the High Shear Solid Phase Peptide Synthesis (HS-SPPS) method, a tripeptide synthesis was used as a model in which the two methods were compared. The selected transformation was a coupling reaction of an amino-protected amino acid to a dipeptide connected to a resin, thus forming a resin comprising a tripeptide. Specifically, the model peptide to be synthesized was Fmoc-L-His-Phe-Gly-NH$_2$. Therefore, the model reaction consisted of coupling the free amine residue of a resin comprising a glycine (Gly) and phenylalanine (Phe) units (H$_2$N-Phe-Gly-Resin) with the carboxyl residue of a histidine unit protected with trityl (triphenylmethyl-Ph$_3$C) on its heterocyclic nitrogen and with Fmoc (Fluorenylmethyloxycarbonyl) on its primary amine (Fmoc-His(Trt)OH; N$_\alpha$—Fmoc-N$_{(im)}$-trityl-L-histidine; CAS NO 109425-51-6). It is noted that the coupling of Fmoc-His(Trt)OH to H$_2$N-Phe-Gly-Resin, using coupling agents, such as DIPC (N,N'-diisopropyl carbodiimide), DCC (N,N'-dicyclohexylcarbodiimide) and EDC (1-Ethyl-3-(3-dimethylaminopropyl) carbodiimide) without additives or base, is known to cause racemization and leads to reduced yield of the tripeptide. In other words, the coupling of Fmoc-L-His(Trt)OH is considered challenging mainly due to enhanced formation of the diastereomeric peptide side product containing D-Histidine.

In order to monitor the rate of the coupling reaction and the degree of racemization, the two pure diastereomeric peptides (i.e. Fmoc-L-His-Phe-Gly-NH$_2$ and Fmoc-D-His-Phe-Gly-NH$_2$), were separately prepared using known coupling methods. The two pure peptides were examined in HPLC. The examination revealed two separate peaks, which also don't overlap with the HPLC signals of the starting materials, thus allowing the follow-up of both conversion and racemization of the tripeptide product at the same time.

In the experiment, the coupling of Fmoc-His(Trt)OH to H$_2$N-Phe-Gly-Resin was tested in the presence of EDC in NMP solvent (without base or additives) using (i) a traditional shaker apparatus, and (ii) the HS-SPS Apparatus 2. Thereafter, aliquots were taken for "small cleavage" (as described in Falb et al. The Journal of Peptide Research (1999) 53, 507-517) of the product from the resin and samples were examined for degrees of conversion and racemization using HPLC. The results are summarized in Table 5.

TABLE 5

Degrees of conversion and racemization in the coupling of Fmoc-His(Trt)OH to H$_2$N-Phe-Gly-Resin, without additives, using shaker and HS-SPPS conditions.

| Reaction No. | Mixing system | Addition of EDC | Time [minutes] | % conversion | % Disomer | additives |
|---|---|---|---|---|---|---|
| 1 (i) | HS-SPS Apparatus 2 | gradual[1] | 30 | 39.4 | 5.2 | — |
| 1 (ii) | HS-SPS Apparatus 2 | gradual[1] | 90 | 70.6 | 8.5 | — |

TABLE 5-continued

Degrees of conversion and racemization in the coupling of Fmoc-His(Trt)OH to H₂N-Phe-Gly-Resin, without additives, using shaker and HS-SPPS conditions.

| Reaction No. | Mixing system | Addition of EDC | Time [minutes] | % conversion | % Disomer | additives |
|---|---|---|---|---|---|---|
| 2 | shaker | at once[2] | 90 | 0.00 | — | — |
| 3 | shaker | at once[3] | 90 | 61.0 | 44.0 | — |

[1]EDC was added gradually by micro syringe.
[2]The coupling did not progress and a symmetrical histidine anhydride was formed.
[3]Addition of histidine anhydride at once to the resin suspension.

From Table 5 it is evident that Reaction 2, in which EDC was added to a mixture of His(Trt)OH and H₂N-Phe-Gly-Resin in NMP, did not progress to provide any of the target tripeptide within 90 minutes.

Due to the fact that product was not forming in Reaction 2, the symmetrical protected histidine anhydride was prepared separately and was added to a suspension of the H₂N-Phe-Gly-Resin in NMP (Reaction 3). This method allowed 67% conversion after 1.5 hours of reaction, albeit with almost a half of the product being the undesired D diastereomer racemization product.

Surprisingly, under similar reaction conditions of mixing the reactants with EDC in NMP, stirring in an HS-SPS Apparatus, instead of shaking, provided 70% conversion with only 8.5% of the D diastreomer (Reaction 1). Without wishing to be bound to any mechanism, it is suggested that gradual addition of the EDC, which is possible in the method of the present invention, but not in the other method, resulted in more efficient and faster coupling reaction and reduced racemization and other side reactions. This possibly due to elimination of accumulation of reactants or intermediates in the reaction mixture. The fact that in both under HS-SPS conditions and the shaker the conversion was the same (58.4%) and it did not reach 100% reflects the known fact that the reaction of the active ester 4 with the peptide-resin is diffusion controlled and therefore cannot be accelerated by stirring.

A similar experiment was conducted with the addition of HOBt (hydroxybenzotriazole) as an additive using HS-SPS Apparatus 2 (Reaction 4) and using a shaker (Reaction 5). The reactions were monitored and the results are provided in Table 6.

TABLE 6

Degrees of conversion and racemization in the coupling of Fmoc-His(Trt)OH to H₂N-Phe-Gly-Resin, with additives, using shaker and HS-SPPS conditions.

| Reaction No. | Mixing system | Time [minutes] | % D isomer | Conversion % | Yield % |
|---|---|---|---|---|---|
| 4 (i) | HS-SPS Apparatus 2[1] | 0 | 0 | 0.0 | 0.0 |
| 4 (ii) | HS-SPS Apparatus 2[1] | 5 | 0 | 0.0 | 0.0 |
| 4 (iii) | HS-SPS Apparatus 2[1] | 15 | 0 | 12.4 | 12.4 |
| 4 (iv) | HS-SPS Apparatus 2[1] | 30 | 0 | 37.5 | 37.5 |
| 4 (v) | HS-SPS Apparatus 2[1] | 45 | 0 | 53.0 | 53.0 |
| 4 (vi) | HS-SPS Apparatus 2[1] | 60 | 0 | 58.4 | 58.4 |
| 5 | Shaker[2] | , 60 min | 5.5 | 55.3 | 52.2 |

[1]DIC was added gradually for 5 minutes by micro syringe.
[2]The DIC added at once and isomer with D-Histidine formed.

From Table 6 it is evident that Reaction 6, in which EDC and HOBt were added to a mixture of His(Trt)OH and H₂N-Phe-Gly-Resin in NMP in a shaker, proceeded to form the product within 90 minutes, but with 5.5% racemization.

Surprisingly, under similar reaction conditions of mixing the reactants with EDC an HOBtin NMP, stirring in an HS-SPS Apparatus, instead of shaking, provided 60% conversion with no D diastreomer witnessed (Reaction 4).

Example 4—Cleavage of Protecting Group

To evaluate the effect of the mixing method on reaction rates occurring on the solid support, cleavage reactions of the primary amine protecting group FMOC were monitored. Fmoc removal typically takes place multiple times during peptide elongation in Fmoc based SPPS and is performed with large amounts of piperidine (20% v/v) in DMF or in NMP. Piperidine has been associated with acute and chronic health effects including eye and skin irritations and damage to mucous membranes. Thus, huge toxic piperidine waste is being produced both in research and in industrial facilities.

Accordingly, Fmoc cleavage progression was monitored under different conditions by spectrophotometrically quantifying the amount of dibenzofulvene liberated. The rate of Fmoc removal from Fmoc Rink amide resin was determined using 5%-20% piperidine solution in NMP in (i) a regular shaker, (ii) a mechanical stirrer at 100 RPM; (iii) a mechanical stirrer at 700 RPM; and (iv) an immobilized reactor. The amount of dibenzofulvene was quantified and normalized compared to the Fmoc content of the resin measured by an Fmoc quantification test.

Figure 10:
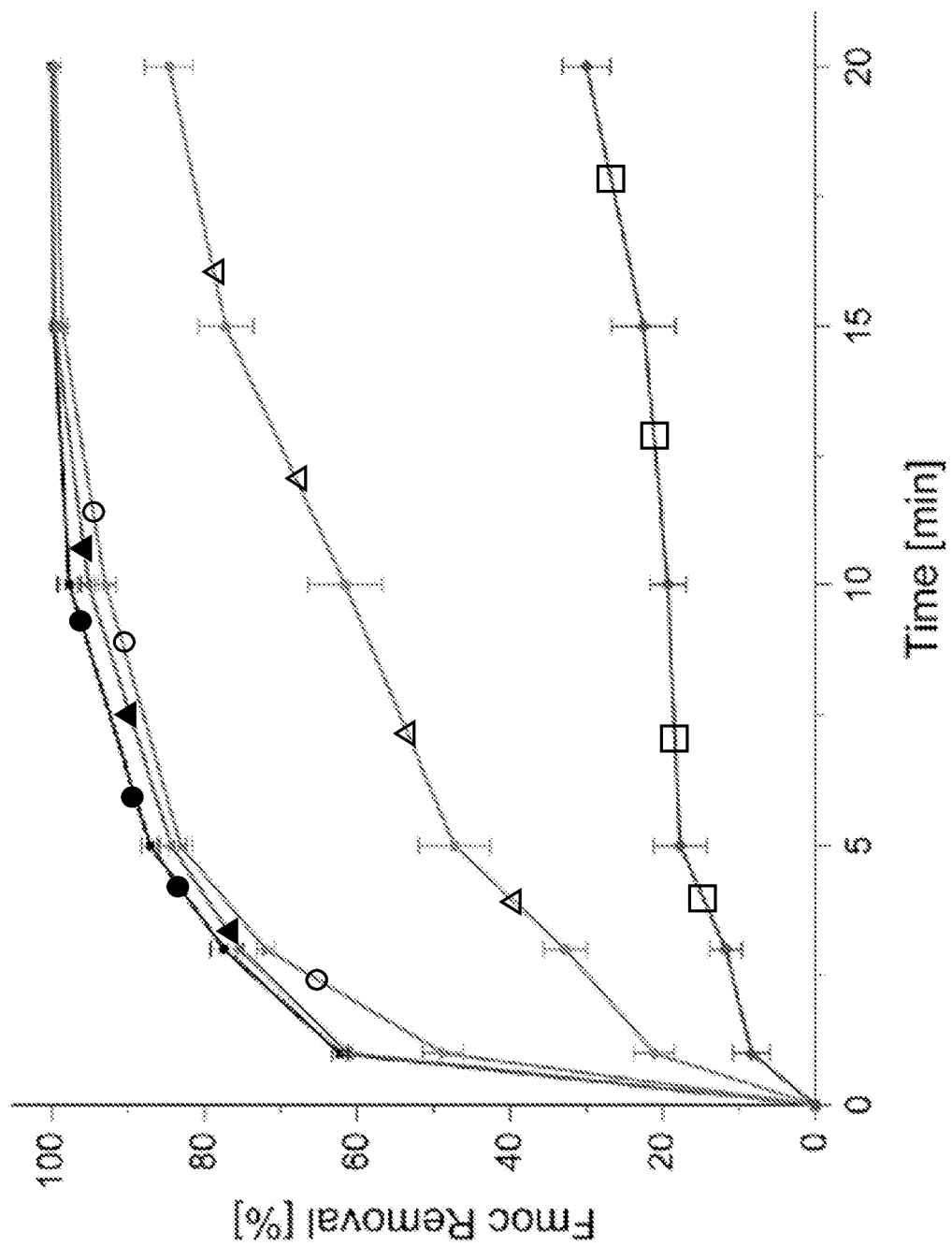
FIG. 10 is a graph showing the % progression of the Fmoc cleavage for a mechanical stirrer apparatus employed at 700 rpm with 5% piperidine (full circles); a shaker apparatus with 5% piperidine (empty triangles); a shaker apparatus with 20% piperidine solution (full triangles); a mechanical stirrer apparatus employed at 100 rpm with 5% piperidine (empty circles); and an immobilized reactor apparatus without mixing, with 5% piperidine (empty squares). The error is the standard deviation between three independent experiments conducted.

FIG. 10 is a graph showing the % progression of the Fmoc cleavage (as determined by dibenzofulvene formation) vs. time, for the following apparatus configurations, and amount of piperidine: mechanical stirrer apparatus employed at 700 rpm with 5% piperidine (full circles); shaker apparatus with 5% piperidine (empty triangles); shaker apparatus with 20% piperidine solution (full triangles); mechanical stirrer apparatus employed at 100 rpm with 5% piperidine (empty circles); immobilized reactor apparatus without mixing, with 5% piperidine (empty squares). The error is the standard deviation between three independent experiments conducted.

As seen in FIG. 10, the UV measurements for formation of dibenzofulvene showed that 95% Fmoc removal was achieved in 20% piperidine/NMP after 10 min reaction in a shaker (full triangles), but only 60% cleavage was obtained after 10 minutes with 5% piperidine/NMP using the same apparatus (empty triangles). Strikingly, the cleavage profiles achieved with 5% piperidine/NMP with two separate mechanical stirring apparatuses (700—full circles; and 100 rpm—empty circles) were almost identical to that achieved with 20% piperidine/NMP in the shaker with both high and low rpm rates of mechanical stirring. As a control, Fmoc removal in immobilized reactor with 5% piperidine/NMP was performed. The amount of Fmoc removed was only 20% after 20 min of reaction, which is significantly lower than the amount removed with overhead stirring (empty squares). Without wishing to be bound by any theory or mechanism of action, it is assumed that the permeation of reagents inside the solid support depends on the mixing properties of the solution. The experiment proved that the reaction rate with a mechanical stirrer using the 5% solution is much faster than using the same solution with a shaker. It is suggested that the higher diffusion rate achieved by mechanical stirring allowed for the local concentration of piperidine to remain high while rapidly dispersing the dibenzofulvene product. Thus, stirring has a combined effect in which both the diffusion to the beads and the permeation inside the beads are increased.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for performing at least one cycle of solid phase synthesis of an organic molecule, the method comprising the steps of:
   i. providing a reactor comprising a reaction chamber and a stirring apparatus, wherein the stirring apparatus comprises an impeller having at least two blades rotatable about an axis;
   ii. inserting beads of functionalized polymeric resin and at least one solvent into the reactor to provide a reaction mixture, wherein the reaction mixture is in contact with the rotatable blades;
   iii. inserting at least one reactant into the reaction chamber;
   iv. spinning the impeller for a period of time, at a rotational rate of at least 600 rounds per minute (rpm), while maintaining a shear rate of at least $3 \cdot 10^3$ sec$^{-1}$;
thereby performing at least one cycle of the solid phase synthesis of the organic molecule.

2. The method of claim 1, wherein the stirring apparatus is a mechanical stirrer and spinning of the impeller is performed at a rotational rate of 600 to 1400 rounds per minute, maintaining a shear rate of at least $3 \cdot 10^3$ sec$^{-1}$.

3. The method of claim 2, wherein the spinning of the impeller comprises maintaining shear stress of at least 1.5 N/m$^2$ in the reaction mixture.

4. The method of claim 1, wherein the stirring apparatus is a homogenizer and spinning of the impeller is performed at a rotational rate of 5,000-30,000 rounds per minutes, maintaining a shear rate of at least $1 \cdot 10^6$ sec$^{-1}$.

5. The method of claim 4, wherein the homogenizer is a rotor-stator homogenizer.

6. The method of claim 1, wherein the functionalized beads of polymeric resin have particle size of 20-200 μm.

7. The method of claim 1, wherein the organic molecule is a polymer comprising a molecule selected from the group consisting of a peptide chain, a nucleotide chain and a sugar.

8. The method of claim 1, wherein the organic molecule comprises a peptide chain.

9. The method of claim 7, for performing a cycle in the solid phase synthesis of a polymeric organic molecule, wherein the method comprises the steps of:
   (a) providing a reactor comprising a reaction chamber and a stirring apparatus comprising an impeller having at least two blades rotatable about an axis;
   (b) inserting beads of functionalized polymeric resin and at least one solvent into the reactor to provide a reaction mixture, wherein the reaction mixture is in contact with the rotatable blades;
   (c) inserting at least one protected monomeric organic molecule and at least one coupling agent into the reaction chamber and spinning the impeller, thereby forming a coupling product of the protected monomeric organic molecule and the resin;
   (d) washing excess of the protected monomeric organic molecule; and
   (e) inserting at least one deprotecting reagent into the reaction chamber and spinning the impeller, thereby removing at least one protecting group from the coupling product, forming a coupling product of the deprotected monomeric organic molecule and the resin, thereby completing a cycle in the solid phase synthesis of a polymeric organic molecule;
wherein the spinning of the impeller in at least one of steps (c) and (e) is performed for a period of time, at a rotational rate of at least 600 rounds per minute, while maintaining a shear rate of at least $3 \cdot 10^3$ sec$^{-1}$, optionally wherein steps (c) to (e) are repeated a plurality of cycles.

10. The method of claim 9, wherein both steps (c) and (e) are performed for a period of time, at a rotational rate of at least 600 rounds per minute, while maintaining a shear rate of at least $3 \cdot 10^3$ sec$^{-1}$.

11. The method of claim 7, wherein the at least one reactant is selected from the group consisting of: a deprotection agent, a coupling agent, and a protected monomeric organic molecule.

12. The method of claim 7, wherein the at least one reactant comprises a coupling agent and a protected monomeric organic molecule, thereby performing at least one coupling cycle of the solid phase synthesis of the organic molecule.

13. The method of claim 12, wherein the protected monomeric organic molecule is an α-N-protected amino acid.

14. The method of claim 7, wherein the reactant comprises at least one deprotecting reagent.

15. The method of claim 1, further comprising the steps of washing the reaction mixture and filtering the beads of polymeric resin.

16. The method of claim 1, further comprising repeating steps (ii) to (iv) at least one more time thereby performing at least one additional cycle of the solid phase synthesis of the organic molecule.

17. The method of claim 16, comprising at least two steps of coupling of an amino acid to the resin and at least two steps of removal of protecting group.

18. The method of claim 7, further comprising the step of cleavage of the polymeric organic molecule from the polymeric resin.

19. The method of claim 1, comprising an initial step of swelling the beads of polymeric resin in at least one solvent.

20. The method of claim 19, wherein swelling the beads of polymeric resin comprises mixing the beads of polymeric resin for a specified period of time in the solvent, at a rotational rate of at least 600 rounds per minute and maintaining shear rate of at least $3 \cdot 10^3$ $\sec^{-1}$.

\* \* \* \* \*